(12) United States Patent
He et al.

(10) Patent No.: US 8,518,311 B2
(45) Date of Patent: Aug. 27, 2013

(54) MULTICOMPONENT BIODEGRADABLE FILAMENTS AND NONWOVEN WEBS FORMED THEREFROM

(75) Inventors: Aimin He, Alpharetta, GA (US); James H. Wang, Appleton, WI (US); Vasily A. Topolkaraev, Appleton, WI (US); Gregory J. Wideman, Menasha, WI (US); Doris Palfery, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 527 days.

(21) Appl. No.: 12/668,255

(22) PCT Filed: Aug. 22, 2007

(86) PCT No.: PCT/IB2007/053351
§ 371 (c)(1),
(2), (4) Date: Nov. 22, 2010

(87) PCT Pub. No.: WO2009/024836
PCT Pub. Date: Feb. 26, 2009

(65) Prior Publication Data
US 2011/0059669 A1    Mar. 10, 2011

(51) Int. Cl.
*D01D 5/32* (2006.01)
*D01D 5/34* (2006.01)
*D01F 8/14* (2006.01)
*D04H 3/00* (2012.01)

(52) U.S. Cl.
USPC ........... 264/103; 264/172.14; 264/172.15; 264/172.17; 264/210.2

(58) Field of Classification Search
USPC ............ 264/103, 172.14, 172.15, 172.17, 264/210.2; 156/167, 181
See application file for complete search history.

(56) References Cited

U.S. PATENT DOCUMENTS

| 3,884,850 A | 5/1975 | Ostrowski |
| 4,434,078 A | 2/1984 | Kaneko |

(Continued)

FOREIGN PATENT DOCUMENTS

| DE | 4200320 A1 | 7/1993 |
| EP | 0731198 A2 | 9/1996 |

(Continued)

OTHER PUBLICATIONS

Article—Cooper-White et al., "Rheological Properties of Poly(lactides). Effect of Molecular Weight and Temperature on the Viscoelasticity of Poly(*l*-lactic acid)," *Journal of Polymer Science: Part B: Polymer Physics*, vol. 37, 1999, pp. 1803-1814.

(Continued)

*Primary Examiner* — Leo B Tentoni
(74) *Attorney, Agent, or Firm* — Dority & Manning, P.A.

(57) ABSTRACT

A biodegradable, substantially continuous filament is provided. The filament contains a first component formed from at least one high melting polyester and a second component formed from at least one low melting polyester. The low melting point polyester is an aliphatic-aromatic copolyester formed by melt blending a polymer and an alcohol to initiate an alcoholysis reaction that results in a copolyester having one or more hydroxyalkyl or alkyl terminal groups. By selectively controlling the alcoholysis conditions (e.g., alcohol and copolymer concentrations, catalysts, temperature, etc.), a modified aliphatic-aromatic copolyester may be achieved that has a molecular weight lower than the starting aliphatic-aromatic polymer. Such lower molecular weight polymers also have the combination of a higher melt flow index and lower apparent viscosity, which is useful in the formation of substantially continuous filaments.

22 Claims, 3 Drawing Sheets

(56) References Cited

U.S. PATENT DOCUMENTS

| | | |
|---|---|---|
| 4,554,344 A | 11/1985 | Jackson, Jr. et al. |
| 4,596,660 A | 6/1986 | Hou |
| 4,797,468 A | 1/1989 | De Vries |
| 4,970,288 A | 11/1990 | Larkin et al. |
| 5,130,073 A | 7/1992 | Meirowitz et al. |
| 5,166,310 A | 11/1992 | Rooney |
| 5,310,599 A | 5/1994 | Ford |
| 5,378,801 A | 1/1995 | Reichert et al. |
| 5,466,517 A | 11/1995 | Eschwey et al. |
| 5,470,944 A | 11/1995 | Bonsignore |
| 5,521,278 A | 5/1996 | O'Brien et al. |
| 5,525,706 A | 6/1996 | Gruber et al. |
| 5,543,494 A | 8/1996 | Perego et al. |
| 5,574,129 A | 11/1996 | Miyoshi et al. |
| 5,593,778 A | 1/1997 | Kondo et al. |
| 5,614,298 A | 3/1997 | Tanaka et al. |
| 5,633,342 A | 5/1997 | Verser et al. |
| 5,714,569 A | 2/1998 | Imaizumi et al. |
| 5,763,564 A | 6/1998 | Gruber et al. |
| 5,770,682 A | 6/1998 | Ohara et al. |
| 5,807,973 A | 9/1998 | Gruber et al. |
| 5,817,721 A | 10/1998 | Warzelhan et al. |
| 5,821,327 A | 10/1998 | Oota et al. |
| 5,844,066 A | 12/1998 | Kakizawa |
| 5,866,677 A | 2/1999 | Maeda et al. |
| 5,880,254 A | 3/1999 | Ohara et al. |
| 5,883,199 A | 3/1999 | McCarthy et al. |
| 5,900,322 A | 5/1999 | Buchanana et al. |
| 5,910,545 A | 6/1999 | Tsai et al. |
| 5,912,275 A | 6/1999 | Hall et al. |
| 5,952,433 A | 9/1999 | Wang et al. |
| 5,965,648 A | 10/1999 | Brink et al. |
| 5,981,694 A | 11/1999 | Gruber et al. |
| 6,045,908 A | 4/2000 | Nakajima et al. |
| 6,063,895 A | 5/2000 | Chung et al. |
| 6,096,855 A | 8/2000 | Sodergard et al. |
| 6,111,060 A | 8/2000 | Gruber et al. |
| 6,117,928 A | 9/2000 | Hiltunen et al. |
| 6,143,863 A | 11/2000 | Gruber et al. |
| 6,177,193 B1 | 1/2001 | Tsai et al. |
| 6,180,287 B1 | 1/2001 | Watanabe et al. |
| 6,194,483 B1 | 2/2001 | Tsai et al. |
| 6,197,237 B1 | 3/2001 | Tsai et al. |
| 6,197,860 B1 | 3/2001 | Tsai et al. |
| 6,201,068 B1 | 3/2001 | Tsai et al. |
| 6,207,617 B1 | 3/2001 | Gillespie |
| 6,218,321 B1 | 4/2001 | Lorcks et al. |
| 6,225,388 B1 | 5/2001 | Tsai et al. |
| 6,235,393 B1 | 5/2001 | Kimura et al. |
| 6,245,831 B1 | 6/2001 | Tsai et al. |
| 6,258,924 B1 | 7/2001 | Warzelhan et al. |
| 6,262,294 B1 | 7/2001 | Sako et al. |
| 6,268,434 B1 | 7/2001 | Tsai et al. |
| 6,326,458 B1 | 12/2001 | Gruber et al. |
| 6,355,772 B1 | 3/2002 | Gruber et al. |
| 6,376,580 B1 | 4/2002 | Ikuta et al. |
| 6,399,716 B2 | 6/2002 | Chung et al. |
| 6,420,027 B2 | 7/2002 | Kimura et al. |
| 6,500,897 B2 | 12/2002 | Wang et al. |
| 6,506,873 B1 | 1/2003 | Ryan et al. |
| 6,521,336 B2 | 2/2003 | Narita et al. |
| 6,552,124 B2 | 4/2003 | Wang et al. |
| 6,562,939 B1 | 5/2003 | Farachi et al. |
| 6,579,934 B1 | 6/2003 | Wang et al. |
| 6,607,996 B1 | 8/2003 | Matsunaga et al. |
| 6,667,385 B2 | 12/2003 | Pierce et al. |
| 6,713,595 B2 | 3/2004 | Chung et al. |
| 6,780,964 B2 | 8/2004 | Satoh et al. |
| 6,787,493 B1 | 9/2004 | Nagaoka et al. |
| 6,787,632 B2 | 9/2004 | Phelps et al. |
| 6,838,403 B2 | 1/2005 | Tsai et al. |
| 6,946,506 B2 | 9/2005 | Bond et al. |
| 6,953,622 B2 | 10/2005 | Tsai et al. |
| 7,037,983 B2 | 5/2006 | Huang et al. |
| 7,053,151 B2 | 5/2006 | Wang et al. |
| 7,067,611 B2 | 6/2006 | Yamane et al. |
| 7,193,032 B2 | 3/2007 | Culbert et al. |
| 7,196,157 B2 | 3/2007 | Bastioli et al. |
| 7,256,223 B2 | 8/2007 | Mohanty et al. |
| 7,288,618 B2 | 10/2007 | Bastioli et al. |
| 7,332,562 B2 | 2/2008 | Chen et al. |
| 7,361,725 B2 | 4/2008 | Yu |
| 7,368,503 B2 | 5/2008 | Hale |
| 2003/0022581 A1 | 1/2003 | Tsai et al. |
| 2003/0204180 A1 | 10/2003 | Huang et al. |
| 2004/0266983 A1 | 12/2004 | Reeve et al. |
| 2009/0203281 A1 | 8/2009 | He et al. |
| 2009/0291607 A1 | 11/2009 | Wang et al. |
| 2009/0311937 A1 | 12/2009 | He et al. |
| 2010/0048081 A1 | 2/2010 | Topolkaraev et al. |
| 2010/0048082 A1 | 2/2010 | Topolkaraev et al. |
| 2010/0323575 A1 | 12/2010 | He et al. |
| 2011/0065573 A1 | 3/2011 | McEneany et al. |

FOREIGN PATENT DOCUMENTS

| | | |
|---|---|---|
| EP | 0731198 A3 | 9/1996 |
| EP | 0755956 A2 | 1/1997 |
| EP | 0755956 A3 | 1/1997 |
| EP | 0905292 A1 | 3/1999 |
| EP | 1215225 A1 | 6/2002 |
| EP | 1236753 A1 | 9/2002 |
| EP | 1345979 B1 | 7/2004 |
| EP | 1000102 B1 | 11/2005 |
| EP | 1497353 B1 | 12/2005 |
| JP | 62156995 A | 7/1987 |
| JP | 7109659 A | 4/1995 |
| JP | 7125128 A | 5/1995 |
| JP | 8193123 A | 7/1996 |
| JP | 8199052 A | 8/1996 |
| JP | 8283557 A | 10/1996 |
| JP | 9241417 A | 9/1997 |
| JP | 11043857 A | 2/1999 |
| JP | 11050369 A | 2/1999 |
| JP | 11117164 A | 4/1999 |
| JP | 11286864 A | 10/1999 |
| JP | 2001136300 A | 5/2000 |
| JP | 2003183934 A | 7/2003 |
| JP | 2005048350 A | 2/2005 |
| KR | 20040005193 A | 1/2004 |
| KR | 20040005194 A | 1/2004 |
| WO | WO 9741165 A1 | 11/1997 |
| WO | WO 9836008 A1 | 8/1998 |
| WO | WO 9850611 A1 | 11/1998 |
| WO | WO 9928368 A1 | 6/1999 |
| WO | WO 0114621 A1 | 3/2001 |
| WO | WO 03089492 A1 | 10/2003 |
| WO | WO 03089493 A1 | 10/2003 |
| WO | WO 2004048471 A1 | 6/2004 |
| WO | WO 2004061172 A2 | 7/2004 |
| WO | WO 2004061172 A3 | 7/2004 |
| WO | WO 2005061617 A1 | 7/2005 |
| WO | WO 2005092948 A2 | 10/2005 |
| WO | WO 2005092948 A3 | 10/2005 |
| WO | WO 2006097353 A1 | 9/2006 |
| WO | WO 2007004906 A1 | 1/2007 |
| WO | WO 2007070064 A1 | 6/2007 |
| WO | WO 2008008067 A1 | 1/2008 |
| WO | WO 2008008068 A1 | 1/2008 |
| WO | WO 2008008074 A1 | 1/2008 |
| WO | WO 2008073099 A1 | 6/2008 |

OTHER PUBLICATIONS

Article—Kulinski et al., "Plasticization of Poly(L-lactide) with Poly(propylene glycol)," *Biomacromolecules*, vol. 7, No. 7, 2006, pp. 2128-2135.

Article—Witt et al., "Biodegradation of aliphatic-aromatic copolyesters: evaluation of the final biodegradability and ecotoxicological impact of degradation intermediates," *Chemosphere* 44, 2001, pp. 289-299.

Search Report and Written Opinion for PCT/US2006/047852 dated Jun. 15, 2007, 15 pages.

MULTICOMPONENT BIODEGRADABLE FILAMENTS AND NONWOVEN WEBS FORMED THEREFROM

BACKGROUND OF THE INVENTION

Biodegradable nonwoven webs are useful in a wide range of applications, such as in the formation of disposable absorbent products (e.g., diapers, training pants, sanitary wipes, feminine pads and liners, adult incontinence pads, guards, garments, etc.) and/or health care products (e.g., surgical gowns, drapes, etc.). To facilitate formation of the nonwoven web, a biodegradable polymer should be selected that is melt processable, yet also has good mechanical and physical properties. Biodegradable aliphatic-aromatic copolyesters have been developed that possess good mechanical and physical properties. Unfortunately, the high molecular weight and viscosity of aliphatic-aromatic copolyesters has generally prevented their use in certain fiber forming processes. For example, conventional aliphatic-aromatic copolyesters are not typically suitable for meltblowing processes, which require a low polymer viscosity for successful microfiber formation. As such, a need currently exists for a biodegradable aliphatic-aromatic copolyester that exhibits good mechanical and physical properties, but which may be readily formed into a nonwoven web using a variety of techniques (e.g., meltblowing).

SUMMARY OF THE INVENTION

In accordance with one embodiment of the present invention, a biodegradable, substantially continuous multicomponent filament is disclosed that comprises a first component and a second component. The first component contains a first polyester having a melting point of from about 150° C. to about 250° C. and the second component contains a second polyester. The second polyester is an aliphatic-aromatic copolyester terminated with an alkyl group, hydroxyalkyl group, or a combination thereof. The aliphatic-aromatic copolyester has a melt flow index of from about 5 to about 200 grams per 10 minutes, determined at a load of 2160 grams and temperature of 190° C. in accordance with ASTM Test Method D1238-E.

In accordance with another embodiment of the present invention, a method for forming biodegradable, substantially continuous multicomponent filaments is disclosed. The method comprises forming a first thermoplastic composition that contains a first polyester having a melting point of from about 150° C. to about 250° C. and forming a second thermoplastic composition by melt blending a precursor aliphatic-aromatic copolyester with at least one alcohol so that the copolyester undergoes an alcoholysis reaction. The alcoholysis reaction results in a modified copolyester having a melt flow index that is greater than the melt flow index of the precursor copolyester, determined at a load of 2160 grams and temperature of 190° C. in accordance with ASTM Test Method D1238-E. The first thermoplastic composition and the second thermoplastic composition are co-extruded to form substantially continuous filaments.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
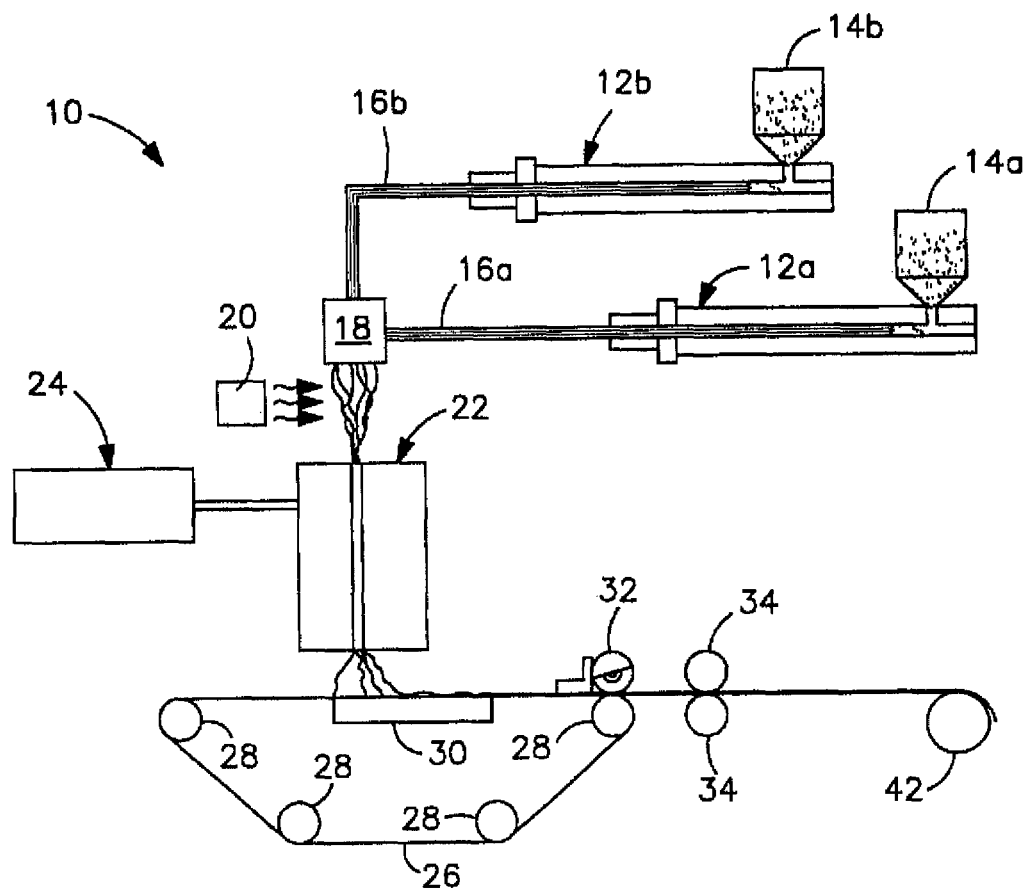
FIG. 1 is a schematic illustration of a process that may be used in one embodiment of the present invention to form a continuous filament web.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Definitions

As used herein, the term "biodegradable" or "biodegradable polymer" generally refers to a material that degrades from the action of naturally occurring microorganisms, such as bacteria, fungi, and algae; environmental heat; moisture; or other environmental factors. The biodegradability of a material may be determined using ASTM Test Method 5338.92.

As used herein, the term "continuous filament web" generally refers to a nonwoven web containing substantially continuous filaments. The filaments may, for example, have a length much greater than their diameter, such as a length to diameter ratio ("aspect ratio") greater than about 15,000 to 1, and in some cases, greater than about 50,000 to 1.

As used herein, the term "nonwoven web" refers to a web having a structure of individual threads (e.g., fibers or filaments) that are randomly interlaid, not in an identifiable manner as in a knitted fabric. Nonwoven webs include, for example, meltblown webs, spunbond webs, carded webs, wet-laid webs, airlaid webs, coform webs, hydraulically entangled webs, etc. The basis weight of the nonwoven web may generally vary, but is typically from about 5 grams per square meter ("gsm") to 200 gsm, in some embodiments from about 10 gsm to about 150 gsm, and in some embodiments, from about 15 gsm to about 100 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous filaments. The filaments are formed by extruding a molten thermoplastic material from a plurality of fine, usually circular, capillaries of a spinnerette with the diameter of the extruded filaments then being rapidly reduced as by, for example, eductive drawing and/or other well-known spunbonding mechanisms. The production of spunbond webs is described and illustrated, for example, in U.S. Pat. Nos. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond filaments are generally not tacky when they are deposited onto a collecting surface. Spunbond filaments may sometimes have diameters less than about 40 micrometers, and are often between about 5 to about 20 micrometers.

As used herein, the term "multicomponent" refers to filaments formed from at least two polymer components (e.g., bicomponent filaments).

Detailed Description

The present invention is directed to a substantially continuous filament that is biodegradable. The filament contains a first component formed from at least one high melting polyester and a second component formed from at least one low melting polyester. The first and second components may be arranged in any desired configuration, such as sheath-core, side-by-side, pie, island-in-the-sea, and so forth. Regardless, the low melting point polyester is an aliphatic-aromatic copolyester formed by melt blending a polymer and an alcohol to initiate an alcoholysis reaction that results in a copolyester having one or more hydroxyalkyl or alkyl terminal groups. By selectively controlling the alcoholysis conditions (e.g., alcohol and copolymer concentrations, catalysts, temperature, etc.), a modified aliphatic-aromatic copolyester may be achieved that has a molecular weight lower than the starting aliphatic-aromatic polymer. Such lower molecular weight polymers also have the combination of a higher melt flow index and lower apparent viscosity, which is useful in the formation of substantially continuous filaments.

I. First Component

As stated, the first component of the multicomponent filaments is formed from one or more "high melting point" biodegradable polyesters. The melting point of such polyesters is from about 150° C. to about 250° C., in some embodiments from about 160° C. to about 240° C., and in some embodiments, from about 170° C. to about 220° C. Various "high melting point" polyesters may be employed in the present invention, such as polyesteramides, modified polyethylene terephthalate, polylactic acid (PLA), terpolymers based on polylactic acid, polyglycolic acid, polyalkylene carbonates (such as polyethylene carbonate), polyhydroxyalkanoates (PHA), polyhydroxybutyrates (PHB), polyhydroxyvalerates (PHV), and polyhydroxybutyrate-hydroxyvalerate copolymers (PHBV). The term "polylactic acid" generally refers to homopolymers of lactic acid, such as poly(L-lactic acid), poly(D-lactic acid), poly(DL-lactic acid), mixtures thereof, and copolymers containing lactic acid as the predominant component and a small proportion of a copolymerizable comonomer, such as 3-hydroxybutyrate, caprolactone, glycolic acid, etc. One particularly suitable polylactic acid polymer that may be used in the present invention is commercially available from Biomer, Inc. (Germany) under the name Biomer™ L9000. Still other suitable polylactic acid polymers are commercially available from Natureworks, LLC of Minneapolis, Minn.

Although not required, the high melting point polyesters typically constitute the principal ingredient of the first component. That is, the polyesters may constitute at least about 80 wt. %, in some embodiments at least about 90 wt. %, and in some embodiments, at least about 95 wt. % of the first component. In such embodiments, the characteristics of the first component (e.g., melting point) will be substantially the same as the characteristics of the polyesters employed. For example, the melting point of the first component may range from about 150° C. to about 250° C., in some embodiments from about 160° C. to about 240° C., and in some embodiments, from about 170° C. to about 220° C.

II. Second Component

The second component is formed from one or more "low melting point" biodegradable aromatic-aliphatic copolyesters. Such copolyesters have a melting point of from about 50° C. to about 150° C., in some embodiments from about 80° C. to about 140° C., and in some embodiments, from about 90° C. to about 130° C. Moreover, the melting point is also typically at least about 30° C., in some embodiments at least about 40° C., and in some embodiments, at least about 50° C. less than the melting point of the "high melting point" polyesters. In addition, they are generally softer to the touch than most "high melting point" polyesters. The glass transition temperature ("$T_g$") of the low melting point copolyesters may also be less than that of the high melting point polyesters to improve flexibility and processability of the polymers. For example, the low melting point copolyesters may have a $T_g$ of about 25° C. or less, in some embodiments about 0° C. or less, and in some embodiments, about −10° C. or less. Such a glass transition temperature may be at least about 5° C., in some embodiments at least about 10° C., and in some embodiments, at least about 15° C. less than the glass transition temperature of the high melting point polyesters. As discussed in more detail below, the melting temperature and glass transition temperature may be determined using differential scanning calorimetry ("DSC") in accordance with ASTM D-3417.

Generally speaking, the aliphatic-aromatic copolyesters are formed by melt blending a polymer an alcohol to initiate an alcoholysis reaction that results in a copolyester having one or more hydroxyalkyl or alkyl terminal groups. Various embodiments of the alcoholysis reaction components and techniques will now be described in more detail below.

III. Reaction Components

A. Aliphatic-Aromatic Copolyester

The aliphatic-aromatic copolyester may be synthesized using any known technique, such as through the condensation polymerization of a polyol in conjunction with aliphatic and aromatic dicarboxylic acids or anhydrides thereof. The polyols may be substituted or unsubstituted, linear or branched, polyols selected from polyols containing 2 to about 12 carbon atoms and polyalkylene ether glycols containing 2 to 8 carbon atoms. Examples of polyols that may be used include, but are not limited to, ethylene glycol, diethylene glycol, propylene glycol, 1,2-propanediol, 1,3-propanediol, 2,2-dimethyl-1,3-propanediol, 1,2- butanediol, 1,3-butanediol, 1,4-butanediol, 1,2-pentanediol, 1,5-pentanediol, 1,6-hexanediol, polyethylene glycol, diethylene glycol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, cyclopentanediol, triethylene glycol, and tetraethylene glycol. Preferred polyols include 1,4-butanediol; 1,3-propanediol; ethylene glycol; 1,6-hexanediol; diethylene glycol; and 1,4-cyclohexanedimethanol.

Representative aliphatic dicarboxylic acids that may be used include substituted or unsubstituted, linear or branched, non-aromatic dicarboxylic acids selected from aliphatic dicarboxylic acids containing 2 to about 12 carbon atoms, and derivatives thereof. Non-limiting examples of aliphatic dicarboxylic acids include malonic, succinic, oxalic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, and 2,5-norbornanedicarboxylic. Representative aromatic dicarboxylic acids that may be used include substituted and unsubstituted, linear or branched, aromatic dicarboxylic acids selected from aromatic dicarboxylic acids containing 1 to about 6 carbon atoms, and derivatives thereof. Non-limiting examples of aromatic dicarboxylic acids include terephthalic acid, dimethyl terephthalate, isophthalic acid, dimethyl isophthalate, 2,6-napthalene dicarboxylic acid, dimethyl-2,6-naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4,4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), etc., and mixtures thereof.

The polymerization may be catalyzed by a catalyst, such as a titanium-based catalyst (e.g., tetraisopropyltitanate, tetraisopropoxy titanium, dibutoxydiacetoacetoxy titanium, or tetrabutyltitanate). If desired, a diisocyanate chain extender may be reacted with the copolyester to increase its molecular weight. Representative diisocyanates may include toluene 2,4-diisocyanate, toluene 2,6-diisocyanate, 2,4'-diphenylmethane diisocyanate, naphthylene-1,5-diisocyanate, xylylene diisocyanate, hexamethylene diisocyanate ("HMDI"), isophorone diisocyanate and methylenebis(2-isocyanatocyclohexane). Trifunctional isocyanate compounds may also be employed that contain isocyanurate and/or biurea groups with a functionality of not less than three, or to replace the diisocyanate compounds partially by tri-or polyisocyanates. The preferred diisocyanate is hexamethylene diisocyanate. The amount of the chain extender employed is typically from about 0.3 to about 3.5 wt. %, in some embodiments, from about 0.5 to about 2.5 wt. % based on the total weight percent of the polymer.

The copolyesters may either be a linear polymer or a long-chain branched polymer. Long-chain branched polymers are generally prepared by using a low molecular weight branching agent, such as a polyol, polycarboxylic acid, hydroxy acid, and so forth. Representative low molecular weight polyols that may be employed as branching agents include glycerol, trimethylolpropane, trimethylolethane, polyethertriols, glycerol, 1,2,4-butanetriol, pentaerythritol, 1,2,6-hexanetriol, sorbitol, 1,1,4,4,-tetrakis(hydroxymethyl)cyclohexane, tris(2-hydroxyethyl)isocyanurate, and dipentaerythritol. Representative higher molecular weight polyols (molecular weight of 400 to 3000) that may be used as branching agents include trials derived by condensing alkylene oxides having 2 to 3 carbons, such as ethylene oxide and propylene oxide with polyol initiators. Representative polycarboxylic acids that may be used as branching agents include hemimellitic acid, trimellitic (1,2,4-benzenetricarboxylic) acid and anhydride, trimesic (1,3,5-benzenetricarboxylic) acid, pyromellitic acid and anhydride, benzenetetracarboxylic acid, benzophenone tetracarboxylic acid, 1,1,2,2-ethane-tetracarboxylic acid, 1,1,2-ethanetricarboxylic acid, 1,3,5-pentanetricarboxylic acid, and 1,2,3,4-cyclopentanetetracarboxylic acid. Representative hydroxy acids that may be used as branching agents include malic acid, citric acid, tartaric acid, 3-hydroxyglutaric acid, mucic acid, trihydroxyglutaric acid, 4-carboxyphthalic anhydride, hydroxyisophthalic acid, and 4-(beta-hydroxyethyl)phthalic acid. Such hydroxy acids contain a combination of 3 or more hydroxyl and carboxyl groups. Especially preferred branching agents include trimellitic acid, trimesic acid, pentaerythritol, trimethylol propane and 1,2,4-butanetriol.

The aromatic dicarboxylic acid monomer constituent may be present in the copolyester in an amount of from about 10 mole % to about 40 mole %, in some embodiments from about 15 mole % to about 35 mole %, and in some embodiments, from about 15 mole % to about 30 mole %. The aliphatic dicarboxylic acid monomer constituent may likewise be present in the copolyester in an amount of from about 15 mole % to about 45 mole %, in some embodiments from about 20 mole % to about 40 mole %, and in some embodiments, from about 25 mole % to about 35 mole %. The polyol monomer constituent may also be present in the aliphatic-aromatic copolyester in an amount of from about 30 mole % to about 65 mole %, in some embodiments from about 40 mole % to about 50 mole %, and in some embodiments, from about 45 mole % to about 55 mole %.

In one particular embodiment, for example, the aliphatic-aromatic copolyester may comprise the following structure:

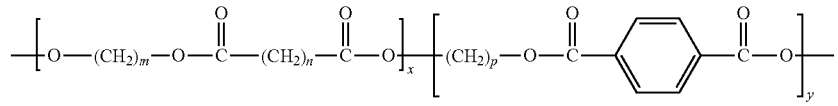

wherein, m is an integer from 2 to 10, in some embodiments from 2 to 4, and in one embodiment, 4;

n is an integer from 0 to 18, in some embodiments from 2 to 4, and in one embodiment, 4;

p is an integer from 2 to 10, in some embodiments from 2 to 4, and in one embodiment, 4;

x is an integer greater than 1; and y is an integer greater than 1. One example of such a copolyester is polybutylene adipate terephthalate, which is commercially available under the designation ECOFLEX® F BX 7011 from BASF Corp. Another example of a suitable copolyester containing an aromatic terephtalic acid monomer constituent is available under the designation ENPOL™ 8060M from IRE Chemicals (South Korea). Other suitable aliphatic-aromatic copolyesters may be described in U.S. Pat. Nos. 5,292,783; 5,446,079; 5,559,171; 5,580,911; 5,599,858; 5,817,721; 5,900,322; and 6,258,924, which are incorporated herein in their entirety by reference thereto for all purposes.

The aliphatic-aromatic polyester typically has a number average molecular weight ("$M_n$") ranging from about 40,000 to about 120,000 grams per mole, in some embodiments from about 50,000 to about 100,000 grams per mole, and in some embodiments, from about 60,000 to about 85,000 grams per mole. Likewise, the polymer also typically has a weight average molecular weight ("$M_w$") ranging from about 70,000 to about 240,000 grams per mole, in some embodiments from about 80,000 to about 190,000 grams per mole, and in some embodiments, from about 100,000 to about 150,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 3.0, in some embodiments from about 1.2 to about 2.0, and in some embodiments, from about 1.4 to about 1.8. The weight and number average molecular weights may be determined by methods known to those skilled in the art.

The aromatic-aliphatic polyester may also have an apparent viscosity of from about 100 to about 1000 Pascal seconds (Pa·s), in some embodiments from about 200 to about 800 Pa·s, and in some embodiments, from about 300 to about 600 Pa·s, as determined at a temperature of 170° C. and a shear rate of 1000 sec$^{-1}$. The melt flow index of the aromatic-aliphatic polyester may also range from about 0.1 to about 10 grams per 10 minutes, in some embodiments from about 0.5 to about 8 grams per 10 minutes, and in some embodiments, from about 1 to about 5 grams per 10 minutes. The melt flow index is the weight of a polymer (in grams) that may be forced through an extrusion rheometer orifice (0.0825-inch diameter) when subjected to a load of 2160 grams in 10 minutes at a certain temperature (e.g., 190° C.), measured in accordance with ASTM Test Method D1238-E.

B. Alcohol

As indicated above, the aliphatic-aromatic copolyester may be reacted with an alcohol to form a modified copolyester having a reduced molecular weight. The concentration of the alcohol reactant may influence the extent to which the molecular weight is altered. For instance, higher alcohol concentrations generally result in a more significant decrease in molecular weight. Of course, too high of an alcohol concentration may also affect the physical characteristics of the resulting polymer. Thus, in most embodiments, the alcohol(s) are employed in an amount of about 0.1 wt. % to about 10 wt. %, in some embodiments from about 0,1 wt. % to about 4 wt. %, and in some embodiments, from about 0.2 wt. % to about 1 wt. %, based on the total weight of the starting aliphatic-aromatic copolyester.

The alcohol may be monohydric or polyhydric (dihydric, trihydric, tetrahydric, etc.), saturated or unsaturated, and optionally substituted with functional groups, such as carboxyl, amine, etc. Examples of suitable monohydric alcohols include methanol, ethanol, 1-propanol, 2-propanol, 1-butanol, 2-butanol, 1-pentanol, 2-pentanol, 3-pentanol, 1-hexanol, 2-hexanol, 3-hexanol, 1-heptanol, 2-heptanol, 3-heptanol, 4-heptanol, 1-octanol, 2-octanol, 3-octanol, 4-octanol, 1-nonanol, 2-nonanol, 3-nonanol, 4-nonanol, 5-nonanol, 1-decanol, 2-decanol, 3-decanol, 4-decanol, 5-decanol, allyl alcohol, 1-butenol, 2-butenol, 1-pentenol, 2-pentenol, 1-hexenol, 2-hexenol, 3-hexenol, 1-heptenol, 2-heptenol, 3-heptenol, 1-octenol, 2-octenol, 3-octenol, 4-octenol, 1-nonenol, 2-nonenol, 3-nonenol, 4-nonenol, 1-decenol, 2-decenol, 3-decenol, 4-decenol, 5-decenol, cyclohexanol, cyclopentanol, cycloheptanol, 1-phenythyl alcohol, 2-phenythyl alcohol, 2-ethoxy-ethanol, methanolamine, ethanolamine, and so forth. Examples of suitable dihydric alcohols include 1,3-propanediol, 1,4-butanediol, 1,5-pentanediol, 1,6-hexanediol, 1,7-heptanediol, 1,8-octanediol, 1,2-cyclohexanedimethanol, 1,3-cyclohexanedimethanol, 1-hydroxymethyl-2-hydroxyethylcyclohexane, 1-hydroxy-2-hydroxypropylcyclohexane, 1-hydroxy-2-hydroxyethylcyclohexane, 1-hydroxymethyl-2-hydroxyethylbenzene, 1-hydroxymethyl-2-hydroxypropylbenzene, 1-hydroxy-2-hydroxyethylbenzene, 1,2-benzylmethylol, 1,3-benzyldimethylol, and so forth. Suitable trihydric alcohols may include glycerol, trimethylolpropane, etc., while suitable tetrahydric alcohols may include pentaerythritol, erythritol, etc. Preferred alcohols are dihydric alcohols having from 2 to 6 carbon atoms, such as 1,3-propanediol and 1,4-butanediol.

The hydroxy group of the alcohol is generally capable of attacking an ester linkage of the aliphatic-aromatic copolyester, thereby leading to chain scission or "depolymerization" of the copolyester molecule into one or more shorter ester chains. The shorter chains may include aliphatic-aromatic polyesters or oligomers, as well as minor portions of aliphatic polyesters or oligomers, aromatic polyesters or oligomers, and combinations of any of the foregoing. Although not necessarily required, the short chain aliphatic-aromatic polyesters formed during alcoholysis are often terminated with an alkyl and/or hydroxyalkyl groups derived from the alcohol. Alkyl group terminations are typically derived from monohydric alcohols, while hydroxyalkyl group terminations are typically derived from polyhydric alcohols. In one particular embodiment, for example, an aliphatic-aromatic copolyester is formed during the alcoholysis reaction that comprises the following general structure:

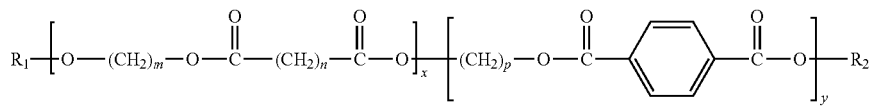

wherein,
m is an integer from 2 to 10, in some embodiments from 2 to 4, and in one embodiment, 4;
n is an integer from 0 to 18, in some embodiments from 2 to 4, and in one embodiment, 4;
p is an integer from 2 to 10, in some embodiments from 2 to 4, and in one embodiment, 4;
x is an integer greater than 1;
y is an integer greater than 1; and
$R_1$ and $R_2$ are independently selected from hydrogen; hydroxyl groups; straight chain or branched, substituted or unsubstituted $C_1$-$C_{10}$ alkyl groups; straight chain or branched, substituted or unsubstituted $C_1$-$C_{10}$ hydroxalkyl groups. Preferably, at least one of $R_1$ and $R_2$, or both, are straight chain or branched, substituted or unsubstituted, $C_1$-$C_{10}$ alkyl or $C_1$-$C_{10}$ hydroxyalkyl groups, in some embodiments $C_1$-$C_8$ alkyl or $C_1$-$C_8$ hydroxyalkyl groups, and in some embodiments, $C_2$-$C_6$ alkyl or $C_2$-$C_6$ hydroxyalkyl groups. Examples of suitable alkyl and hydroxyalkyl groups include, for instance, methyl, ethyl, iso-propyl, n-propyl, n-butyl, isobutyl, sec-butyl, tert-butyl, n-pentyl, n-hexyl, n-heptyl, n-octyl, n-decyl, 1-hydroxyethyl, 2-hydroxyethyl, 3-hydroxypropyl, 4-hydroxybutyl, and 5-hydroxypentyl groups. Thus, as indicated, the modified aliphatic-aromatic copolyester has a different chemical composition than an unmodified copolyester in terms of its terminal groups. The terminal groups may play a substantial role in determining the properties of the polymer, such as its reactivity, stability, etc.

Regardless of its particular structure, a new polymer species is formed during alcoholysis that has a molecular weight lower than that of the starting polyester. The weight average and/or number average molecular weights may, for instance, each be reduced so that the ratio of the starting copolyester molecular weight to the new molecular weight is at least about 1.1, in some embodiments at least about 1.4, and in some embodiments, at least about 1.6. For example, the modified aliphatic-aromatic copolyester may have a number average molecular weight ("$M_n$") ranging from about 10,000 to about 70,000 grams per mole, in some embodiments from about 20,000 to about 60,000 grams per mole, and in some embodiments, from about 30,000 to about 55,000 grams per mole. Likewise, the modified copolyester may also have a weight average molecular weight ("$M_w$") of from about 20,000 to about 125,000 grams per mole, in some embodiments from about 30,000 to about 110,000 grams per mole, and in some embodiments, from about 40,000 to about 90,000 grams per mole.

In addition to possessing a lower molecular weight, the modified aliphatic-aromatic copolyester may also have a lower apparent viscosity and higher melt flow index than the starting polyester. The apparent viscosity may for instance, be reduced so that the ratio of the starting copolyester viscosity to the modified copolyester viscosity is at least about 1.1, in some embodiments at least about 2, and in some embodiments, from about 10 to about 40. Likewise, the melt flow index may be increased so that the ratio of the modified copolyester melt flow index to the starting copolyester melt flow index is at least about 1.5, in some embodiments at least about 3, in some embodiments at least about 10, and in some embodiments, from about 20 to about 200. In one particular embodiment, the modified copolyester may have an apparent viscosity of from about 10 to about 500 Pascal seconds (Pa·s), in some embodiments from about 20 to about 400 Pa·s, and in some embodiments, from about 30 to about 250 Pa·s, as determined at a temperature of 170° C. and a shear rate of 1000 sec$^{-1}$. The melt flow index (190° C., 2.16 kg) of the modified copolyester may range from about 5 to about 200 grams per 10 minutes, in some embodiments from about 10 to about 100 grams per 10 minutes, and in some embodiments, from about 15 to about 50 grams per 10 minutes. Of course, the extent to which the molecular weight, apparent viscosity, and/or melt flow index are altered by the alcoholysis reaction may vary depending on the intended application.

Although differing from the starting polymer in certain properties, the modified copolyester may nevertheless retain other properties of the starting polymer to enhance the flexibility and processability of the polymers. For example, the thermal characteristics (e.g., $T_g$, $T_m$, and latent heat of fusion) typically remain substantially the same as the starting polymer, such as within the ranges noted above. Further, even though the actual molecular weights may differ, the polydispersity index of the modified copolyester may remain substantially the same as the starting polymer, such as within the range of about 1.0 to about 3.0, in some embodiments from about 1.1 to about 2.0, and in some embodiments, from about 1.2 to about 1.8.

Typically, modified aliphatic-aromatic copolyesters constitute the principal ingredient of the second component. That is, the modified copolyesters may constitute at least about 90 wt. %, in some embodiments at least about 92 wt. %, and in some embodiments, at least about 95 wt. % of the second component. In such embodiments, the characteristics of the second component (e.g., melting point) will be substantially the same as the characteristics of the modified copolyesters employed.

C. Catalyst

A catalyst may be employed to facilitate the modification of the alcoholysis reaction. The concentration of the catalyst may influence the extent to which the molecular weight is altered. For instance, higher catalyst concentrations generally result in a more significant decrease in molecular weight. Of course, too high of a catalyst concentration may also affect the physical characteristics of the resulting polymer. Thus, in most embodiments, the catalyst(s) are employed in an amount of about 50 to about 2000 parts per million ("ppm"), in some embodiments from about 100 to about 1000 ppm, and in some embodiments, from about 200 to about 1000 ppm, based on the weight of the starting aliphatic-aromatic copolyester.

Any known catalyst may be used in the present invention to accomplish the desired reaction. In one embodiment, for example, a transition metal catalyst may be employed, such as those based on Group IVB metals and/or Group IVA metals (e.g., alkoxides or salts). Titanium-, zirconium-, and/or tin-based metal catalysts are especially desirable and may include, for instance, titanium butoxide, titanium tetrabutoxide, titanium propoxide, titanium isopropoxide, titanium phenoxide, zirconium butoxide, dibutyltin oxide, dibutyltin diacetate, tin phenoxide, tin octylate, tin stearate, dibutyltin dioctoate, dibutyltin dioleylmaleate, dibutyltin dibutylmaleate, dibutyltin dilaurate, 1,1,3,3-tetrabutyl-1,3-dilauryloxy-carbonyldistannoxane, dibutyltindiacetate, dibutyltin diacetylacetonate, dibutyltin bis(o-phenylphenoxide), dibutyltin bis(triethoxysilicate), dibutyltin distearate, dibutyltin bis(isononyl-3-mercaptopropionate), dibutyltin bis(isooctyl thioglycolate), dioctyltin oxide, dioctyltin dilaurate, dioctyltin diacetate, and dioctyltin diversatate.

D. Co-Solvent

The alcoholysis reaction is typically carried out in the absence of a solvent other than the alcohol reactant. Nevertheless, a co-solvent may be employed in some embodiments of the present invention. In one embodiment, for instance, the co-solvent may facilitate the dispersion of the catalyst in the reactant alcohol. Examples of suitable co-solvents may include ethers, such as diethyl ether, anisole, tetrahydrofuran, ethylene glycol dimethyl ether, triethylene glycol dimethyl ether, tetraethylene glycol dimethyl ether, dioxane, etc.; alcohols, such as methanol, ethanol, n-butanol, benzyl alcohol, ethylene glycol, diethylene glycol, etc.; phenols, such as phenol, etc.; carboxylic acids, such as formic acid, acetic acid, propionic acid, toluic acid, etc.; esters, such as methyl acetate, butyl acetate, benzyl benzoate, etc.; aromatic hydrocarbons, such as benzene, toluene, ethylbenzene, tetralin, etc.; aliphatic hydrocarbons, such as n-hexane, n-octane, cyclohexane, etc.; halogenated hydrocarbons, such as dichloromethane, trichloroethane, chlorobenzene, etc.; nitro compounds, such as nitromethane, nitrobenzene, etc.; carbamides, such as N,N-dimethylformamide, N,N-dimethylacetamide, N-methylpyrrolidone, etc.; ureas, such as N,N-dimethylimidazolidinone, etc.; sulfones, such as dimethyl sulfone, etc.; sulfoxides, such as dimethyl sulfoxide, etc.; lactones, such as butyrolactone, caprolactone, etc.; carbonic acid esters, such as dimethyl carbonate, ethylene carbonate, etc.; and so forth.

When employed, the co-solvent(s) may be employed in an amount from about 0.5 wt. % to about 20 wt. %, in some embodiments from about 0.8 wt. % to about 10 wt. %, and in some embodiments, from about 1 wt. % to about 5 wt %, based on the weight of the reactive composition. It should be understood, however, that a co-solvent is not required. In fact, in some embodiments of the present invention, the reactive composition is substantially free of any co-solvents, e.g., less than about 0.5 wt. % of the reactive composition.

E. Other Ingredients

Other ingredients may of course be utilized for a variety of different reasons. For instance, a wetting agent may be employed in some embodiments of the present invention to improve hydrophilicity. Wetting agents suitable for use in the present invention are generally compatible with aliphatic-aromatic copolyesters. Examples of suitable wetting agents may include surfactants, such as UNITHOX® 480 and UNITHOX® 750 ethoxylated alcohols, or UNICID™ acid amide ethoxylates, all available from Petrolite Corporation of Tulsa, Okla. Other suitable wetting agents are described in U.S. Pat. No. 6,177,193 to Tsai, et al., which is incorporated herein in its entirety by reference thereto for all relevant purposes. Still other materials that may be used include, without limitation, melt stabilizers, processing stabilizers, heat stabilizers, light stabilizers, antioxidants, pigments, surfactants, waxes, flow promoters, plasticizers, particulates, and other materials added to enhance processability. When utilized, such additional ingredients are each typically present in an amount of less than about 5 wt. %, in some embodiments less than about 1 wt. %, and in some embodiments, less than about 0.5 wt. %, based on the weight of the aliphatic-aromatic copolyester starting polymer.

IV. Reaction Techniques

The alcoholysis reaction may be performed using any of a variety of known techniques. In one embodiment, for example, the reaction is conducted while the starting polymer is in the melt phase ("melt blending") to minimize the need for additional solvents and/or solvent removal processes. The raw materials (e.g., biodegradable polymer, alcohol, catalyst, etc.) may be supplied separately or in combination (e.g., in a solution). The raw materials may likewise be supplied either simultaneously or in sequence to a melt-blending device that dispersively blends the materials. Batch and/or continuous melt blending techniques may be employed. For example, a mixer/kneader, Banbury mixer, Farrel continuous mixer, single-screw extruder, twin-screw extruder, roll mill, etc., may be utilized to blend the materials. One particularly suitable melt-blending device is a co-rotating, twin-screw extruder (e.g., ZSK-30 twin-screw extruder available from Werner & Pfleiderer Corporation of Ramsey, N.J.). Such extruders may include feeding and venting ports and provide high intensity distributive and dispersive mixing, which facilitate the alcoholysis reaction. The raw materials (e.g., polymer, alcohol, catalyst, etc.) may be fed into the extruder from a hopper. The raw materials may be provided to the hopper using any conventional technique and in any state. For example, the alcohol may be supplied as a vapor or liquid. Alternatively, the aliphatic-aromatic copolyester may be fed to the hopper, and the alcohol and optional catalyst (either in combination or separately) may be injected into the copolyester melt in the extruder downstream from the hopper.

Regardless of the particular melt blending technique chosen, the raw materials are blended under high shear/pressure and heat to ensure sufficient mixing for initiating the alcoholysis reaction. For example, melt blending may occur at a temperature of from about 50° C. to about 300° C., in some embodiments, from about 70° C. to about 250° C., and in some embodiments, from about 90° C. to about 220° C. Likewise, the apparent shear rate during melt blending may range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows.

V. Substantially Continuous Filaments

Any of a variety of known techniques may be employed to form substantially continuous filaments in accordance with the present invention. A modified aliphatic-aromatic copolyester may be initially formed and then fed to an extruder in a filament formation line (e.g., extruder 12 of a spinning line). Alternatively, the modified aliphatic-aromatic copolymer may be directly formed into a filament. Referring to FIG. 1, for example, one embodiment of a process 10 for forming a substantially continuous filament in accordance with the present invention is shown. As illustrated, the process 10 of this embodiment is arranged to produce a bicomponent, continuous filament web, although it should be understood that other embodiments are contemplated by the present invention. The process 10 employs a pair of extruders 12a and 12b for separately extruding a first component A (e.g., high melting point polymer component) and a second component B (e.g., low melting point polymer component). The relative amount of the components A and B may generally vary based on the desired properties. For example, the first component A normally constitutes from about 5 wt. % to about 95 wt. %, in some embodiments from about 10 wt. % to about 90 wt. %, and in some embodiments, from about 15 wt. % to about 85 wt. % of the multicomponent filaments. Likewise, the second component B normally constitutes from about 5 wt. % to about 95 wt. %, in some embodiments from about 10 wt. % to about 90 wt. %, and in some embodiments, from about 15 wt. % to about 85 wt. % of the multicomponent filaments.

The first component A is fed into the respective extruder 12a from a first hopper 14a and the second component B is fed into the respective extruder 12b from a second hopper 14b. The components A and B are fed from the extruders 12a and 12b ("co-extruded") through respective polymer conduits 16a and 16b to a spinneret 18. Spinnerets for extruding multicomponent filaments are well known to those of skill in the art. For example, the spinneret 18 may include a housing containing a spin pack having a plurality of plates stacked one on top of each other and having a pattern of openings arranged to create flow paths for directing polymer components A and B separately through the spinneret 18. The spinneret 18 also has openings arranged in one or more rows. The openings form a downwardly extruding curtain of filaments when the polymers are extruded therethrough. The spinneret 18 may be arranged to form sheath/core, side-by-side, pie, or other configurations.

The process 10 also employs a quench blower 20 positioned adjacent the curtain of filaments extending from the spinneret 18. Air from the quench air blower 20 quenches the filaments extending from the spinneret 18. The quench air may be directed from one side of the filament curtain as shown in FIG. 1 or both sides of the filament curtain. A fiber draw unit or aspirator 22 is positioned below the spinneret 18 and receives the quenched filaments. Fiber draw units or aspirators for use in melt spinning polymers are well-known in the art. Suitable fiber draw units for use in the process of the present invention include a linear fiber aspirator of the type shown in U.S. Pat. Nos. 3,802,817 and 3,423,255, which are incorporated herein in their entirety by reference thereto for all relevant purposes. The fiber draw unit 22 generally includes an elongate vertical passage through which the filaments are drawn by aspirating air entering from the sides of the passage and flowing downwardly through the passage. A heater or blower 24 supplies aspirating air to the fiber draw unit 22. The aspirating air draws the filaments and ambient air through the fiber draw unit 22. Thereafter, the filaments are formed into a coherent web structure by randomly depositing the filaments onto a forming surface 26 (optionally with the aid of a vacuum) and then bonding the resulting web using any known technique.

To initiate filament formation, the hoppers 14a and 14b are initially filled with the respective components A and B. Components A and B are melted and extruded by the respective extruders 12a and 12b through polymer conduits 16a and 16b and the spinneret 18. Due to the relatively low apparent viscosity of the modified aliphatic-aromatic copolyesters used in the present invention, lower extrusion temperatures may be employed. For example, the extruder 12b for Component B may employ one or multiple zones operating at a temperature of from about 120° C. to about 200° C., and in some embodiments, from about 145° C. to about 195° C. Likewise, the extruder 12a for Component A may employ one or multiple zones operating at a temperature of from about 160° C. to about 250° C., and in some embodiments, from about 190° C. to about 225° C. Typical shear rates range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$.

As the extruded filaments extend below the spinneret 18, a stream of air from the quench blower 20 at least partially quenches the filaments. Such a process generally reduces the temperature of the extruded polymers at least about 100° C. over a relatively short time frame (seconds). This will generally reduce the temperature change needed upon cooling, to preferably be less than 150° C. and, in some cases, less than 100° C. The ability to use relatively low extruder temperature in the present invention also allows for the use of lower quenching temperatures. For example, the quench blower 20 may employ one or more zones operating at a temperature of from about 20° C. to about 100° C., and in some embodiments, from about 25° C. to about 60° C. After quenching, the filaments are drawn into the vertical passage of the fiber draw unit 22 by a flow of a gas such as air, from the heater or blower 24 through the fiber draw unit. The flow of gas causes the filaments to draw or attenuate which increases the molecular orientation or crystallinity of the polymers forming the filaments. The filaments are deposited through the outlet opening of the fiber draw unit 22 and onto a foraminous surface 26. Due to the high strength of the filaments of the present invention, high draw ratios (e.g., linear speed of the foraminous surface 26 divided by the melt pump rate of the extruders 12a and 12b) may be employed in the present invention. For example, the draw ratio may be from about 200:1 to about 6000:1, in some embodiments from about 500:1 to about 5000:1, and in some embodiments, from about 1000:1 to about 4000:1.

The desired denier of the filaments may vary depending on the desired application. Typically, the filaments are formed to have a denier per filament of less than about 6, in some embodiments less than about 3, and in some embodiments, from about 0.5 to about 3. In addition, the filaments generally have an average diameter not greater than about 100 microns, in some embodiments from about 0.5 microns to about 50 microns, and in some embodiments, from about 4 microns to about 40 microns. The ability to produce such filaments may be facilitated in the present invention through the use of a modified copolyester having the desirable combination of low apparent viscosity and high melt flow index.

If desired, an endless foraminous forming surface 26 may be positioned below the fiber draw unit 22 and receive the filaments from an outlet opening. The forming surface 26 travels around guide rollers 28. A vacuum 30 positioned below the forming surface 26 to draw the filaments against the forming surface 26 and consolidate the unbonded nonwoven web. The web may then be compressed by a compression roller 32. Once formed, the nonwoven web may be bonded using any conventional technique, such as with an adhesive or autogenously (e.g., fusion and/or self-adhesion of the filaments without an applied external adhesive). Autogenous bonding, for instance, may be achieved through contact of the filaments while they are semi-molten or tacky, or simply by blending a tackifying resin and/or solvent with the aliphatic polyester(s) used to form the filaments. Suitable autogenous bonding techniques may include ultrasonic bonding, thermal bonding, through-air bonding, and so forth.

In FIG. 1, for instance, the web passes through a nip formed between a pair of rolls 34 prior to being wound onto a roll 42. One or both of the rolls 34 may be heated to melt-fuse the filaments and/or contain intermittently raised bond points to provide an intermittent bonding pattern. The pattern of the raised points may be selected so that the nonwoven web has a total bond area of less than about 50% (as determined by conventional optical microscopic methods), and in some embodiments, less than about 30%. Likewise, the bond density is also typically greater than about 100 bonds per square inch, and in some embodiments, from about 250 to about 500 pin bonds per square inch. Such a combination of total bond area and bond density may be achieved by bonding the web with a pin bond pattern having more than about 100 pin bonds per square inch that provides a total bond surface area less than about 30% when fully contacting a smooth anvil roll. In some embodiments, the bond pattern may have a pin bond density from about 250 to about 350 pin bonds per square inch and a total bond surface area from about 10% to about 25% when contacting a smooth anvil roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., U.S. Design Pat. No. 428,267 to Romano et al. and U.S. Design Pat. No. 390,708 to Brown, which are incorporated herein in their entirety by reference thereto for all purposes.

Due to the particular rheological and thermal properties of the components used to form the multicomponent filaments, the web bonding conditions (e.g., temperature and nip pressure) may be selected to cause the low melting point, modified copolyester to melt and flow without substantially melting the high melting point polyester. For example, the bonding temperature (e.g., the temperature of the rollers 34) may be from about 50° C. to about 160° C., in some embodiments from about 80° C. to about 160° C., and in some embodiments, from about 100° C. to about 140° C. Likewise, the nip pressure may range from about 5 to about 150 pounds per square inch, in some embodiments, from about 10 to about 100 pounds per square inch, and in some embodiments, from about 30 to about 60 pounds per square inch.

When bonded in this mariner, the low melting point, modified copolyester may thus form a matrix within the compacted area that substantially surrounds the high melting point polymer. Because the high melting point polymer does not substantially melt, however, it retains a substantially fibrous form. The high melting point polymer is also generally oriented within the compacted area in two or more directions due to the random manner in which the filaments are deposited. One polymer, for instance, may be oriented from about 60° to about 120°, and in some cases, about 90°, relative to another polymer within a compacted area. In this manner, the high melting point polymer may impart enhanced strength and toughness to the resulting web. For example, the nonwoven web may exhibit a relatively high "peak load", which indicates the maximum load to break as expressed in units of grams-force per inch. The MD peak load of the web may, for instance, be at least about 3000 grams-force per inch ("$g_f$/in"), in some embodiments at least about 3500 $g_f$/in, and in some embodiments, at least about 4000 $g_f$/in. The CD peak load may also be at least about 1200 grams-force per inch ("$g_f$/in"), in some embodiments at least about 1500 $g_f$/in, and in some embodiments, at least about 2500 $g_f$/in.

In addition to contributing to the overall strength of the web, the selected bond conditions may also improve other mechanical properties of the web. For example, although retaining its fiber form within a compacted area, the high melting point polymer will normally release or separate from the compacted area upon the application of strain, rather than fracture. By releasing under strain, the polymer may continue to function as a load bearing member even after the web has exhibited substantial elongation. In this regard, the nonwoven web is capable of exhibiting improved "peak elongation" properties, i.e., the percent elongation of the web at its peak load. For example, the nonwoven web may exhibit a machine direction ("MD") peak elongation of at least about 10%, in some embodiments at least about 20%, and in some embodiments, at least about 35%. The nonwoven web may also exhibit a cross-machine direction ("CD") peak elongation of at least about 35%, in some embodiments at least about 45%, and in some embodiments, at least about 50%. Of course, in addition to possessing good mechanical properties, the nonwoven web is also soft, drapable, and tactile. Further, the nonwoven web possesses good water absorption characteristics, which facilitates its ability to be used in absorbent articles.

The filaments of the present invention may constitute the entire fibrous component of the nonwoven web or blended with other types of fibers (e.g., staple fibers, continuous filaments, etc). When blended with other types of fibers, it is normally desired that the filaments of the present invention constitute from about 20 wt % to about 95 wt. %, in some embodiments from about 30 wt. % to about 90 wt %, and in some embodiments, from about 40 wt. % to about 80 wt. % of the total amount of fibers employed in the nonwoven web. For example, additional monocomponent and/or multicomponent synthetic fibers may be utilized in the nonwoven web. Some suitable polymers that may be used to form the synthetic fibers include, but are not limited to: polyolefins, e.g., polyethylene, polypropylene, polybutylene, and so forth; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; etc. If desired, biodegradable polymers, such as poly(glycolic acid) (PGA), polylactic acid) (PLA), poly(β-malic acid) (PMLA), poly(ε-caprolactone) (PCL), poly(p-dioxanone) (PDS), poly(butylene succinate) (PBS), and poly(3-hydroxybutyrate) (PHB), may also be employed. Some examples of known synthetic fibers include sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth.

The filaments of the present invention may also be blended with pulp fibers, such as high-average fiber length pulp, low-average fiber length pulp, or mixtures thereof. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas fir, true firs, pine (e.g., southern pines), spruce (e.g., black spruce), combinations thereof, and so forth. Northern softwood kraft pulp fibers may be used in the present invention. An example of commercially available southern softwood kraft pulp fibers suitable for use in the present invention include those available from Weyerhaeuser Company with offices in Federal Way, Wash. under the trade designation of "NB-416." Another suitable pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability.

Nonwoven laminates may also be formed in which one or more layers are formed from the multicomponent filaments of the present invention. In one embodiment, for example, the nonwoven laminate contains a meltblown layer positioned between two spunbond layers to form a spunbond/meltblown/spunbond ("SMS") laminate. If desired, one or more of the spunbond layers may be formed from the filaments of the present invention. The meltblown layer may be formed from the modified copolyester, other biodegradable polymer(s), and/or any other polymer (e.g., polyolefins). Various techniques for forming SMS laminates are described in U.S. Pat. Nos. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., as well as U.S. Patent Application Publication No. 2004/0002273 to Fitting, et al., all of which are incorporated herein in their entirety by reference thereto for all purposes. Of course, the nonwoven laminate may have other configuration and possess any desired number of meltblown and spunbond layers, such as spunbond/meltblown/ meltblown/spunbond laminates ("SMMS"), spunbond I meltblown laminates ("SM"), etc. Although the basis weight of the nonwoven laminate may be tailored to the desired application, it generally ranges from about 10 to about 300 grams per square meter ("gsm"), in some embodiments from about 25 to about 200 gsm, and in some embodiments, from about 40 to about 150 gsm.

If desired, the nonwoven web or laminate may be applied with various treatments to impart desirable characteristics. For example, the web may be treated with liquid-repellency additives, antistatic agents, surfactants, colorants, antifogging agents, fluorochemical blood or alcohol repellents, lubricants, and/or antimicrobial agents. In addition, the web may be subjected to an electret treatment that imparts an electrostatic charge to improve filtration efficiency. The charge may include layers of positive or negative charges trapped at or near the surface of the polymer, or charge clouds stored in the bulk of the polymer. The charge may also include polarization charges that are frozen in alignment of the dipoles of the molecules. Techniques for subjecting a fabric to an electret treatment are well known by those skilled in the art. Examples of such techniques include, but are not limited to, thermal, liquid-contact, electron beam and corona discharge techniques. In one particular embodiment, the electret treatment is a corona discharge technique, which involves subjecting the laminate to a pair of electrical fields that have opposite polarities. Other methods for forming an electret material are described in U.S. Pat. Nos. 4,215,682 to Kubik. et al.; U.S. Pat. No. 4,375,718 to Wadsworth; U.S. Pat. No. 4,592,815 to Nakao; U.S. Pat. No. 4,874,659 to Ando; U.S. Pat. No. 5,401,446 to Tsai, et al.; U.S. Pat. No. 5,883,026 to Reader, et al.; U.S. Pat. No. 5,908,598 to Rousseau, et al.; U.S. Pat. No. 6,365,088 to Knight, et al., which are incorporated herein in their entirety by reference thereto for all purposes.

The nonwoven web or laminate may be used in a wide variety of applications. For example, the web may be incorporated into a "medical product", such as gowns, surgical drapes, facemasks, head coverings, surgical caps, shoe coverings, sterilization wraps, warming blankets, heating pads, and so forth. Of course, the nonwoven web may also be used in various other articles. For example, the nonwoven web may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches, and so forth. Materials and processes suitable for forming such articles are well known to those skilled in the art. Absorbent articles, for instance, typically include a substantially liquid-impermeable layer (e.g., outer cover), a liquid-permeable layer (e.g., bodyside liner, surge layer, etc.), and an absorbent core. In one embodiment, for example, a nonwoven web formed according to the present invention may be used to form an outer cover of an absorbent article. If desired, the nonwoven web may be laminated to a liquid-impermeable film that is either vapor-permeable or vapor-impermeable.

The present invention may be better understood with reference to the following examples.

Test Methods

Molecular Weight:

The molecular weight distribution of a polymer was determined by gel permeation chromatography ("GPC"). The samples were initially prepared by adding 0.5% wt/v solutions of the sample polymers in chloroform to 40-milliliter glass vials. For example, 0.05±0.0005 grams of the polymer was added to 10 milliliters of chloroform. The prepared samples were placed on an orbital shaker and agitated overnight. The dissolved sample was filtered through a 0.45-micrometer PTFE membrane and analyzed using the following conditions:

| | |
|---|---|
| Columns: | Styragel HR 1, 2, 3, 4, & 5E (5 in series) at 41° C. |
| Solvent/Eluent: | Chloroform @1.0 milliliter per minute |
| HPLC: | Waters 600E gradient pump and controller, Waters 717 auto sampler |
| Detector: | Waters 2414 Differential Refractometer at sensitivity = 30, at 40° C. and scale factor of 20 |
| Sample Concentration: | 0.5% of polymer "as is" |
| Injection Volume: | 50 microliters |
| Calibration Standards: | Narrow MW polystyrene, 30-microliter injected volume. |

Number Average Molecular Weight ($MW_n$), Weight Average Molecular Weight ($MW_w$) and first moment of viscosity average molecular weight ($MW_z$) were obtained.

Apparent Viscosity:

The rheological properties of polymer samples were determined using a Göttfert Rheograph 2003 capillary rheometer with WinRHEO version 2.31 analysis software. The setup included a 2000-bar pressure transducer and a 30/1:0/180 roundhole capillary die. Sample loading was done by alternating between sample addition and packing with a ramrod. A 2-minute melt time preceded each test to allow the polymer to completely melt at the test temperature (usually 160 to 220° C.). The capillary rheometer determined the apparent viscosity (Pa·s) at various shear rates, such as 100, 200, 500, 1000, 2000, and 4000 $s^{-1}$. The resultant rheology curve of apparent shear rate versus apparent viscosity gave an indication of how the polymer would run at that temperature in an extrusion process.

Melt Flow Index:

The melt flow index is the weight of a polymer (in grams) forced through an extrusion rheometer orifice (0.0825-inch diameter) when subjected to a load of 2160 grams in 10 minutes, typically at 190° C. Unless otherwise indicated, the melt flow index was measured in accordance with ASTM Test Method D1238-E.

Thermal Properties:

The melting temperature ("$T_m$"), glass transition temperature ("$T_g$"), and latent heat of fusion ("$\Delta H_f$") were determined by differential scanning calorimetry (DSC). The differential scanning calorimeter was a THERMAL ANALYST 2910 Differential Scanning Calorimeter, which was outfitted with a liquid nitrogen cooling accessory and with a THERMAL ANALYST 2200 (version 8.10) analysis software program, both of which are available from T.A. Instruments Inc. of New Castle, Del. To avoid directly handling the samples, tweezers or other tools were used. The samples were placed into an aluminum pan and weighed to an accuracy of 0.01 milligram on an analytical balance. A lid was crimped over the material sample onto the pan. Typically, the resin pellets were placed directly in the weighing pan, and the fibers were cut to accommodate placement on the weighing pan and covering by the lid.

The differential scanning calorimeter was calibrated using an indium metal standard and a baseline correction was performed, as described in the operating manual for the differential scanning calorimeter. A material sample was placed into the test chamber of the differential scanning calorimeter for testing, and an empty pan is used as a reference. All testing was run with a 55-cubic centimeter per minute nitrogen (industrial grade) purge on the test chamber. For resin pellet samples, the heating and cooling program was a 2-cycle test that began with an equilibration of the chamber to −50° C., followed by a first heating period at a heating rate of 10° C. per minute to a temperature of 200° C., followed by equilibration of the sample at 200° C. for 3 minutes, followed by a first cooling period at a cooling rate of 10° C. per minute to a temperature of −50° C., followed by equilibration of the sample at −50° C. for 3 minutes, and then a second heating period at a heating rate of 10° C. per minute to a temperature of 200° C. For fiber samples, the heating and cooling program was a 1-cycle test that began with an equilibration of the chamber to −50° C., followed by a heating period at a heating rate of 10° C. per minute to a temperature of 200° C., followed by equilibration of the sample at 200° C. for 3 minutes, and then a cooling period at a cooling rate of 10° C. per minute to a temperature of −50° C., All testing was run with a 55-cubic centimeter per minute nitrogen (industrial grade) purge on the test chamber.

The results were then evaluated using the THERMAL ANALYST 2200 (version 8.10) analysis software program, which identified and quantified the glass transition temperature of inflection, the endothermic and exothermic peaks, and the areas under the peaks on the DSC plots. The glass transition temperature was identified as the region on the plot-line where a distinct change in slope occurred, and the melting temperature was determined using an automatic inflection calculation. The areas under the peaks on the DSC plots were determined in terms of joules per gram of sample (J/g). For example, the heat of fusion of a resin or fiber sample was determined by integrating the area of the endothermic peak. The area values were determined by converting the areas under the DSC plots (e.g. the area of the endotherm) into the units of joules per gram (J/g) using computer software.

Fiber Tenacity:

Individual fiber specimens were carefully extracted from an unbonded portion of a fiber web in a manner that did not significantly pull on the fibers. These fiber specimens were shortened (e.g. cut with scissors) to 38 millimeters in length, and placed separately on a black velvet cloth. 10 to 15 fiber specimens were collected in this manner. The fiber specimens were then mounted in a substantially straight condition on a rectangular paper frame having external dimension of 51 millimeters×51 millimeters and internal dimension of 25 millimeters×25 millimeters. The ends of each fiber specimen were operatively attached to the frame by carefully securing the fiber ends to the sides of the frame with adhesive tape. Each fiber specimen was then be measured for its external, relatively shorter, cross-fiber dimension employing a conventional laboratory microscope, which has been properly calibrated and set at 40× magnification. This cross fiber dimension was recorded as the diameter of the individual fiber specimen. The frame helped to mount the ends of the sample fiber specimens in the upper and lower grips of a constant rate of extension type tensile tester in a manner that avoided excessive damage to the fiber specimens.

A constant rate of extension type of tensile tester and an appropriate load cell were employed for the testing. The load cell was chosen (e.g. 10N) so that the test value fell within 10-90% of the full scale load. The tensile tester (i.e., MTS SYNERGY 200) and load cell were obtained from MTS Systems Corporation of Eden Prairie, Mich. The fiber specimens in the frame assembly were then mounted between the grips of the tensile tester such that the ends of the fibers were operatively held by the grips of the tensile tester. Then, the sides of the paper frame that extended parallel to the fiber length were cut or otherwise separated so that the tensile tester applied the test force only to the fibers. The fibers were then subjected to a pull test at a pull rate and grip speed of 12 inches per minute. The resulting data was analyzed using a TESTWORKS 4 software program from the MTS Corporation with the following test settings:

| Calculation Inputs | | Test Inputs | |
|---|---|---|---|
| Break mark drop | 50% | Break sensitivity | 90% |
| Break marker elongation | 0.1 in | Break threshold | 10 $g_f$ |
| Nominal gage length | 1 in | Data Acq. Rate | 10 Hz |
| Slack pre-load | 1 $lb_f$ | Denier length | 9000 m |
| Slope segment length | 20% | Density | 1.25 g/cm$^3$ |
| Yield offset | 0.20% | Initial speed | 12 in/min |
| Yield segment length | 2% | Secondary speed | 2 in/min |

The tenacity values were expressed in terms of gram-force per denier.

EXAMPLE 1

An aliphatic-aromatic copolyester resin was initially obtained from BASF under the designation ECOFLEX® F BX 7011. The copolyester resin was modified by melt blending with a reactant solution. For Samples 1 and 4 (see Table 1), the reactant solution contained 89 wt. % 1,4-butanediol and 11 wt. % acetone. For Samples 2, 3, 5, and 6 (see Table 1), the reactant solution contained 87 wt. % 1,4-butanediol, 11 wt. % acetone, and 2 wt. % dibutyltin diacetate (the catalyst). The solution was fed by an Eldex pump to a liquid injection port located at barrel #4 of a co-rotating, twin-screw extruder (USALAB Prism H16, diameter: 16 mm, L/D of 40/1) manufactured by Thermo Electron Corporation. The resin was fed to the twin screw extruder at barrel #1. The screw length was 25 inches. The extruder had one die opening having a diameter of 3 millimeters. Upon formation, the extruded resin was cooled on a fan-cooled conveyor belt and formed into pellets by a Conair pelletizer. Reactive extrusion parameters were monitored on the USALAB Prism H16 extruder during the reactive extrusion process. The conditions are shown below in Table 1.

TABLE 1

Reactive Extrusion Process Conditions for modifying
Ecoflex F BX 7011 on a USALAB Prism H16

| Sample No. | Temperature (° C.) Zone 1, 2, 3-8, 9, 10 | | | | | Screw Speed (rpm) | Resin Rate (lb/h) | Reactant (% of resin rate) |
|---|---|---|---|---|---|---|---|---|
| F BX 7011 | 90 | 125 | 165 | 125 | 110 | 150 | 2.6 | 0 |
| 1 | 90 | 125 | 165 | 125 | 110 | 150 | 2.6 | 4 (No catalyst) |
| 2 | 90 | 125 | 165 | 125 | 110 | 150 | 2.6 | 4 |
| 3 | 90 | 125 | 180 | 125 | 110 | 150 | 2.6 | 4 |
| 4 | 90 | 125 | 190 | 125 | 110 | 150 | 2.6 | 4 (No catalyst) |
| 5 | 90 | 125 | 190 | 125 | 110 | 150 | 2.6 | 4 |
| 6 | 90 | 125 | 200 | 125 | 110 | 150 | 2.6 | 4 |

Figure 2:
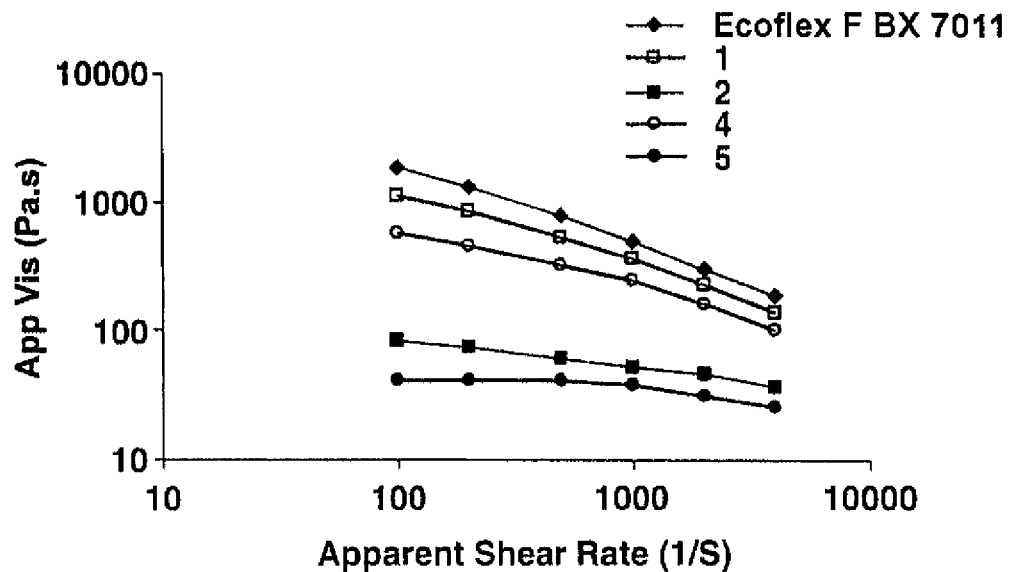
FIG. 2 is a graph depicting apparent viscosity versus various shear rates for the extruded resins of Example 1.

The melt rheology was studied for the unmodified ECOFLEX® F BX 7011 and Samples 1-6 (modified with 1,4 butanediol). The measurement was carried out on a Göettfert Rheograph 2003 (available from Göettfert of Rock Hill, S.C.) at 170° C. with a 30/1(Length/Diameter) mm/mm die. The apparent melt viscosity was determined at apparent shear rates of 100, 200, 500, 1000, 2000 and 5000 $s^{-1}$. The apparent melt viscosities at the various apparent shear rates were plotted and the rheology curves were generated as shown in FIG. 2. As illustrated, the apparent viscosity of the control sample (unmodified ECOFLEX® resin) was much higher than the apparent viscosities of Samples 1-6. The melt flow indices of the samples were also determined with a Tinius Olsen Extrusion plastometer (170° C., 2.16 kg). Further, the samples were subjected to molecular weight (MW) analysis by GPC with narrow MW distribution polystyrenes as standards. The results are set forth below in Table 2.

butanediol. The resulting modified aliphatic-aromatic copolyesters had hydroxybutyl terminal groups.

EXAMPLE 2

The modification of ECOFLEX® F BX 7011 by monohydric alcohols was demonstrated with 1-butanol, 2-propanol, and 2-ethoxy-ethanol as examples of monohydric alcohols.

TABLE 2

Properties of modified Ecoflex F BX 7011 on a USALAB Prism H16

| Sample No. | Apparent Viscosity (Pa · s at apparent shear rate of 1000/s) | Melt Flow rate (g/10 min at 170° C. and 2.16 kg) | Average Mol. Wt (g/mol) | | Polydispersity (Mw/Mn) |
|---|---|---|---|---|---|
| | | | Mw | Mn | |
| F BX 7011 | 498 | 1.65 | 125206 | 73548 | 1.7 |
| 1 | 365 | 9.6 | 114266 | 67937 | 1.68 |
| 2 | 51 | 230 | 77391 | 41544 | 1.86 |
| 3 | 37 | 377 | 71072 | 39767 | 1.79 |
| 4 | 241 | 14 | 109317 | 66507 | 1.64 |
| 5 | 38 | 475 | 65899 | 35529 | 1.85 |
| 6 | 22 | 571 | 56809 | 29316 | 1.94 |

As indicated, the melt flow indices of the modified resins (Samples 1-6) were significantly greater than the control sample. In addition, the weight average molecular weight ($M_w$) and number average molecular weight ($M_n$) were decreased in a controlled fashion, which confirmed that the increase in melt flow index was due to alcoholysis with The experimental set-up was the same as described in Example 1. The process conditions are shown in Table 3. Dibutyltin diacetate was the catalyst used. As shown in Table 3, the torque decreased as monohydric alcohol was fed to the extruder. The torque was further decreased as monohydric alcohol and catalyst were both fed to the extruder.

TABLE 3

Reactive Extrusion Conditions for modifying Ecoflex F BX 7011 on a USALAB Prism H16 with monohydric alcohols

| Sample I.D. | Temperature (° C.) Zone 1, 2, 3-8, 9, 10 | | | | | Screw Speed (rpm) | Resin Rate (lb/h) | Reactant (% of resin rate) | Catalyst (% of resin rate) | Torque (%) |
|---|---|---|---|---|---|---|---|---|---|---|
| F BX 7011 | 90 | 125 | 180 | 125 | 110 | 150 | 2.5 | 0 | 0 | >100 |
| 7 | 90 | 125 | 180 | 125 | 110 | 150 | 2.5 | 3.4%, 2-Propanol | 0 | 90 |
| 8 | 90 | 125 | 180 | 125 | 110 | 150 | 2.5 | 3.4%, 2-Propanol | 0.1 | 80 |
| 9 | 90 | 125 | 180 | 125 | 110 | 150 | 2.5 | 3.6%, 1-Butanol | 0 | 72 |
| 10 | 90 | 125 | 180 | 125 | 110 | 150 | 2.5 | 3.6%, 1-Butanol | 0.1 | 54 |
| 11 | 90 | 125 | 180 | 125 | 110 | 150 | 2.5 | 4%, 2-Ethoxy-ethanol | 0 | 64 |
| 12 | 90 | 125 | 180 | 125 | 110 | 150 | 2.5 | 4%, 2-Ethoxy-ethanol | 0.1 | 58 |

The apparent viscosity and molecular weight were determined for each sample as described in Example 1. The results are shown below in Table 4.

TABLE 4

Properties of modified Ecoflex F BX 7011 with monohydric alcohols on a USALAB Prism H16

| Sample I.D. | Apparent Viscosity (Pa · s at apparent shear rate of 1000 1/s) | Average Mol. Wt (g/mol) Mw | Mn | Polydispersity (Mw/Mn) |
|---|---|---|---|---|
| F BX 7011 | 376 | 128100 | 77200 | 1.66 |
| 7 | 364 | 120800 | 71800 | 1.68 |
| 8 | 273 | 115000 | 69400 | 1.66 |
| 9 | 292 | 115900 | 70800 | 1.64 |
| 10 | 126 | 89800 | 51000 | 1.76 |
| 11 | 324 | 116800 | 71000 | 1.64 |
| 12 | 215 | 104100 | 60500 | 1.72 |

As indicated, Samples 7-12 had lower apparent viscosities and molecular weights over the entire range of shear rates than the control sample. The resulting modified copolyesters had alkyl terminal groups that are compositionally different than the unmodified copolyester.

EXAMPLE 3

Modification of ECOFLEX® F BX 7011 with 1,4-butanediol was performed as described in Example 1 using titanium propoxide ("Ti-P"), titanium butoxide ("Ti-B") and titanium isopropoxide ("Ti-IsoP") catalysts. During the reactive extrusion process, the torques of the extruder were moderately decreased with the addition of only 1,4-butanediol, and further decreased with the addition of the titanium catalysts. The process conditions are shown in Table 5. The resulting modified copolyesters have hydroxybutyl terminal groups.

TABLE 5

Reactive Extrusion Process Conditions for modifying Ecoflex F BX 7011 on a USALAB Prism H16 with 1,4-butanediol and titanium catalysts

| Sample I.D. | Temperature (° C.) Zone 1, 2, 3-8, 9, 10 | | | | Screw Speed (rpm) | Resin Rate (lb/h) | 1,4-butanediol (% of resin rate) | Catalyst (ppm of resin rate) | Torque (%) |
|---|---|---|---|---|---|---|---|---|---|
| F BX 7011 | 95 | 145 | 180 | 130 | 100 | 150 | 3 | 0 | 0 | >100 |
| 13 | 95 | 145 | 180 | 130 | 100 | 150 | 3 | 2 | 0 | 85 |
| 14 | 95 | 145 | 180 | 130 | 100 | 150 | 3 | 3.5 | 0 | 75 |
| 15 | 95 | 145 | 180 | 130 | 100 | 150 | 3 | 2 | 400, Ti-P | 69 |
| 16 | 95 | 145 | 180 | 130 | 100 | 150 | 3 | 3.5 | 700, Ti-P | 48 |
| 17 | 95 | 145 | 180 | 130 | 100 | 150 | 3 | 2 | 400, Ti-B | 76 |
| 18 | 95 | 145 | 180 | 130 | 100 | 150 | 3 | 3.5 | 700, Ti-B | 55 |
| 19 | 95 | 145 | 180 | 130 | 100 | 150 | 3 | 2 | 400, Ti-IsoP | 79 |
| 20 | 95 | 145 | 180 | 130 | 100 | 150 | 3 | 3.5 | 700, Ti-IsoP | 64 |

Figure 3:
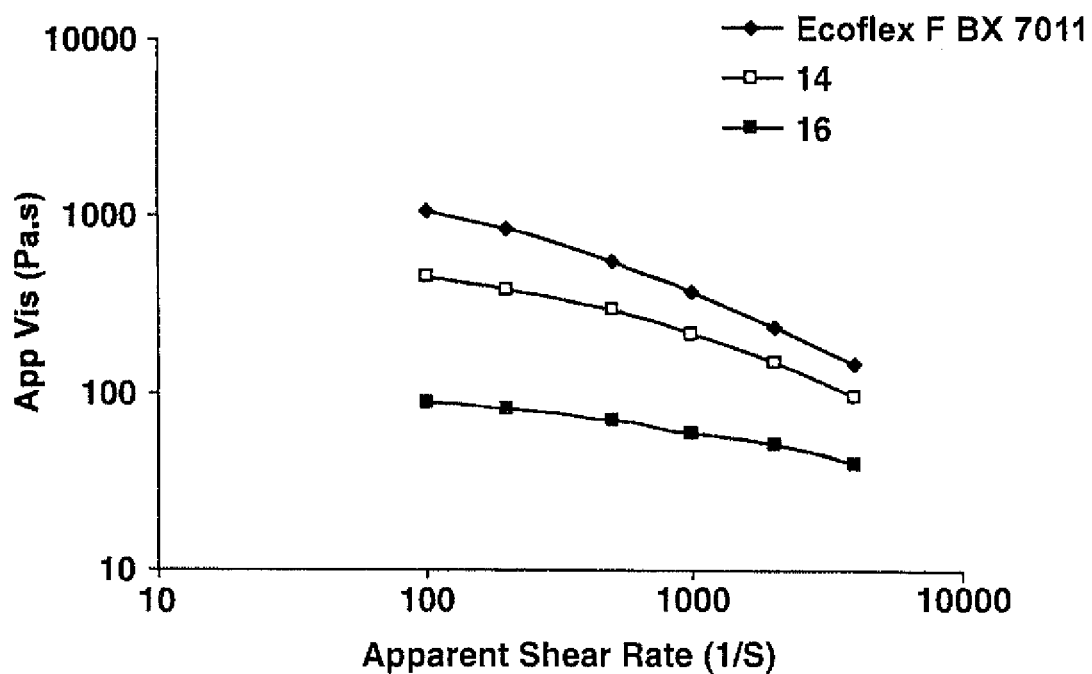
FIG. 3 is a graph depicting apparent viscosity versus various shear rates for the extruded resins of Example 3.

The apparent viscosity and molecular weight were determined for each sample as described in Example 1. The results are shown in FIG. 3 and Table 6.

TABLE 6

Properties of modified Ecoflex F BX 7011 with monohydric alcohols on a USALAB Prism H16

| Sample I.D. | Apparent Viscosity (Pa · s at apparent shear rate of 1000 1/s) | Average Mol. Wt (g/mol) Mw | Mn | Polydispersity (Mw/Mn) |
|---|---|---|---|---|
| F BX 7011 | 376 | 128100 | 77200 | 1.66 |
| 13 | 297 | 112800 | 71000 | 1.7 |
| 14 | 219 | 102000 | 60100 | 1.83 |
| 15 | 198 | 97050 | 57050 | 1.74 |
| 16 | 60 | 69100 | 37600 | 1.67 |
| 17 | 218 | 103700 | 61800 | 1.6 |
| 18 | 95 | 89900 | 51600 | 1.7 |
| 19 | 243 | 110200 | 64100 | 1.68 |
| 20 | 87 | 100300 | 59900 | 1.72 |

As shown in FIG. 3, the viscosity of Sample 16 (titanium propoxide catalyst) was significant lower than Sample 14 (no catalyst) over the entire range of shear rates. In addition, the molecular weights of Samples 13-20 were less than the control sample.

EXAMPLE 4

An aliphatic-aromatic copolyester resin was obtained from BASF under the designation ECOFLEX® F BX 7011. A reactant solution contained 87.5 wt. % 1,4-butanediol, 7.5 wt. % ethanol, and 5 wt. % titanium propoxide was made. A co-rotating, twin-screw extruder was employed (ZSK-30, diameter of 30 millimeters) that was manufactured by Werner and Pfleiderer Corporation of Ramsey, N.J. The screw length was 1328 millimeters. The extruder had 14 barrels, numbered consecutively 1-14 from the feed hopper to the die. The first barrel (#1) received the ECOFLEX® F BX 7011 resin via a volumetric feeder at a throughput of 30 pounds per hour. The fifth barrel (#5) received the reactant solution via a pressurized injector connected with an Eldex pump at a final rate of 0 to 1 wt. % 1,4-butanediol and 0 to 700 parts per million ("ppm") titanium propoxide, respectively. The screw speed was 150 revolutions per minute ("rpm"). The die used to extrude the resin had 4 die openings (6 millimeters in diameter) that were separated by 3 millimeters. Upon formation, the extruded resin was cooled on a fan-cooled conveyor belt and formed into pellets by a Conair pelletizer. Reactive extrusion parameters were monitored during the reactive extrusion process. The conditions are shown below in Table 7.

increase in melt flow index was due to alcoholysis with butanediol catalyzed. Table 9, which is set forth below, also lists the data from DSC analysis of the control sample and Samples 21-23.

TABLE 7

Process Conditions for Reactive Extrusion of Ecoflex F BX 7011 with 1,4-Butanediol on a ZSK-30 Extruder

| Samples No. | Resin feeding rate (lb/h) | Reactants | | Extruder speed (rpm) | Extruder temperature profile (° C.) | | | | | | | | | Torque (%) |
|---|---|---|---|---|---|---|---|---|---|---|---|---|---|---|
| | | Butanediol (%) | Titanium Propoxide (ppm) | | $T_1$ | $T_2$ | $T_3$ | $T_4$ | $T_5$ | $T_6$ | $T_7$ | $T_{melt}$ | $P_{melt}$ | |
| F BX 7011 | 30 | 0 | 0 | 150 | 160 | 170 | 185 | 185 | 185 | 185 | 100 | 116 | 400 | >100 |
| 21 | 30 | 1 | 0 | 150 | 160 | 171 | 184 | 185 | 185 | 185 | 100 | 108 | 300 | >100 |
| 22 | 30 | 0.75 | 375 | 150 | 160 | 170 | 185 | 185 | 185 | 185 | 100 | 110 | 70 | 85-90 |
| 23 | 30 | 1 | 700 | 150 | 160 | 170 | 185 | 185 | 185 | 185 | 100 | 110 | 30 | 66-72 |

As indicated, the addition of 1 wt. % butanediol alone (Sample 21) did not significantly decrease the torque of the control sample, although the die pressure did drop from 300 to 130 pounds per square inch ("psi"). With the addition of 1 wt. % 1,4-butanediol and 700 ppm titanium propoxide (Sample 23), both the torque and die pressure decreased significantly to 66-72% and 30 psi, respectively. The torque and die pressure could be proportionally adjusted with the change of reactant and catalyst.

Figure 4:
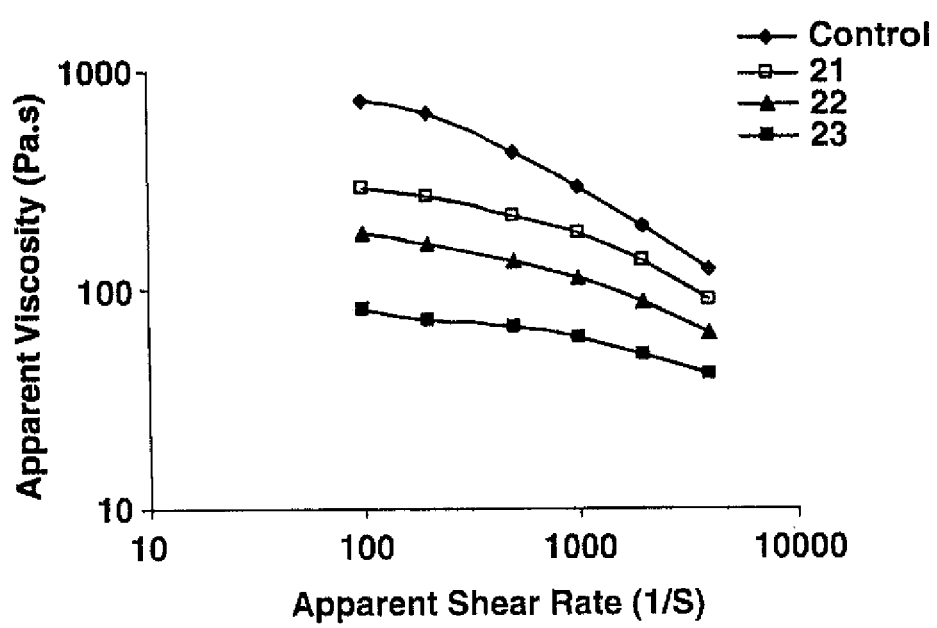
FIG. 4 is a graph depicting apparent viscosity versus various shear rates for the extruded resins of Example 4.

Melt rheology tests were also performed with the control sample and Samples 21-23 on a Göettfert Rheograph 2003 (available from Göettfert in Rock Hill, S.C.) at 180° C. and 190° C. with 30/1 (Length/Diameter) mm/mm die. The apparent melt viscosity was determined at apparent shear rates of 100, 200, 500, 1000, 2000 and 4000 s$^{-1}$. The results are shown in FIG. 4. As indicated, Samples 21-23 had much lower apparent viscosities over the entire range of shear rates than the control sample. The melt flow index of the sample was determined by the method of ASTM D1239, with a Tinius Olsen Extrusion Plastometer at 190° C. and 2.16 kg. Further, the samples were subjected to molecular weight (MW) analysis by GPC with narrow MW polystyrenes as standards. The results are set forth below in Table 8.

TABLE 9

| | DSC Analysis | | |
|---|---|---|---|
| Sample | Glass transition temperature, $T_g$ (° C.) | Melting Peak Temperature, $T_m$ (° C.) | Enthalpy of melting (J/g) |
| Ecoflex ® F BX 7011 | −30.1 | 123.3 | 11.7 |
| Control | −31.5 | 123.5 | 10.1 |
| 21 | −35.1 | 127 | 10.7 |
| 22 | −32.5 | 124.7 | 11.6 |
| 23 | −34.2 | 125.1 | 12 |

As indicated, Samples 22 and 23 (modified with 1,4-butanediol) exhibited little change in their $T_g$ and $T_m$ compared with the control samples.

EXAMPLE 5

As described in Example 4, a ZSK-30 extruder was used to form various samples (Samples 24-28). For Sample 24, the first barrel (#1) received 90 wt. % ECOFLEX® F BX 7011 resin via a volumetric feeder, and the seventh barrel (#7) received 10 wt. % boron nitride via a side feeder, at a total

TABLE 8

Properties of unmodified and modified Ecoflex F BX 7011 on a ZSK-30

| Sample No. | Apparent Viscosity (Pa · s at apparent shear rate of 1000/s at 180° C.) | Melt Flow rate (g/10 min at 190° C. and 2.16 kg) | Average Mol. Wt (g/mol) | | Polydispersity (Mw/Mn) |
|---|---|---|---|---|---|
| | | | Mw | Mn | |
| F BX 7011 | 321 | 4.5 | 125200 | 73500 | 1.7 |
| Control | 294 | 6.8 | 117900 | 72100 | 1.64 |
| 21 | 182 | 24 | 100400 | 60500 | 1.66 |
| 22 | 112 | 68 | 82800 | 46600 | 1.78 |
| 23 | 61 | 169 | 68900 | 37600 | 1.83 |

As indicated, the melt flow indices of the modified resins (Samples 21-23) were significantly greater than the control sample. In addition, the weight average molecular weight ($M_w$) and number average molecular weight ($M_n$) were decreased in a controlled fashion, which confirmed that the throughput of 20 pounds per hour. For Sample 25, the first barrel (#1) received 80 wt. % ECOFLEX® F BX 7011 resin and 20% EnPol® polybutylene succinate G-4500 via two volumetric feeders, at a total throughput of 20 pounds per hour. For Sample 26, the first barrel (#1) received 90 wt. %

ECOFLEX® F BX 7011 resin and 10 wt. % ENMAT® polyhydroxybutyrate-co-valerate via two volumetric feeders, at a total throughput of 30 pounds per hour. For Sample 27, the first barrel (#1) received 85 wt. % ECOFLEX® F BX 7011 resin and 10 wt. % Biomer® polyhydroxybutyrate P-226 via two volumetric feeders, and seventh barrel (#7) received 5% (w/w) boron nitride via a side feeder, at a total throughput of 20 pounds per hour. Finally, for Sample 28, the first barrel (#1) received 90 wt. % ECOFLEX® F BX 7011 resin and 10 wt. % Sample 27 via two volumetric feeders at a total throughput of 30 lb/h, and the fifth barrel (#5) received a reactant solution via a pressurized injector connected with an Eldex pump at a final rate of 0.5 wt. % 1,4-butanediol and 350 parts per million ("ppm") titanium propoxide, respectively.

The die used to extrude the resins had 4 die openings (6 millimeters in diameter) that were separated by 3 millimeters. Upon formation, the extruded resin was cooled on a fan-cooled conveyor belt and formed into pellets by a Conair pelletizer. Reactive extrusion parameters were monitored and recorded. The conditions are shown below in Table 10.

diacetate (DBDA) was injected into the extruder by an Eldex pump via a liquid injection port located at barrel #4, at a total throughput of 3 pounds per hour. For Sample 31, a dry blend of 90 wt. % ECOFLEX® F BX 7011 and 10 wt. % Sample 24 was fed into the extruder at Barrel #1, and a reactant solution of 2.7 wt. % of 1,4-butanediol and 700 ppm of dibutylene diacetate (DBDA) was injected into the extruder by an Eldex pump via a liquid injection port located at Barrel #4, at a total throughput of 3 pounds per hour. For Sample 32, a dry blend of 90 wt. % ECOFLEX® F BX 7011 and 10 wt. % Sample 26 was fed into the extruder at Barrel #1, and a reactant solution of 2.7 wt. % of 1,4-butanediol and 700 ppm of dibutylene diacetate (DBDA) was injected into extruder by an Eldex pump via a liquid injection port located at Barrel #4, at a total throughput of 3 pounds per hour. The extruder profiles were monitored and recorded. The conditions are shown below in Table 11.

TABLE 10

Process Conditions on a ZSK-30 Extruder

| Samples No. | Resin feeding rate (lb/h) | Reactants Butanediol (%) | Reactants Titanium Propoxide (ppm) | Extruder speed (rpm) | $T_1$ | $T_2$ | $T_3$ | $T_4$ | $T_5$ | $T_6$ | $T_7$ | $T_{melt}$ | $P_{melt}$ | Torque (%) |
|---|---|---|---|---|---|---|---|---|---|---|---|---|---|---|
| 24 | 20 | N/A | N/A | 150 | 150 | 160 | 180 | 180 | 180 | 175 | 170 | 192 | 120 | 95 |
| 25 | 20 | N/A | N/A | 150 | 150 | 155 | 170 | 170 | 170 | 170 | 160 | 180 | 220 | 85 |
| 26 | 30 | N/A | N/A | 150 | 150 | 180 | 180 | 185 | 180 | 180 | 165 | 181 | 95 | 75 |
| 27 | 20 | N/A | N/A | 160 | 130 | 180 | 180 | 180 | 180 | 180 | 115 | 127 | 180 | 90 |
| 28 | 30 | 0.5 | 350 | 160 | 150 | 190 | 190 | 190 | 190 | 190 | 125 | 137 | 70 | 88 |

EXAMPLE 6

As described in Example 1, a USALAB Prism H16 extruder was used to prepare various samples (Samples 29-32) for evaluating their fiber spinning capacity. For Sample 29, ECOFLEX® F BX 7011 resin was fed into extruder at Barrel #1, and a reactant solution of 2.7 wt. % of

TABLE 11

Reactive extrusion process conditions for producing modified Ecoflex BFX 7011

| Sample I.D. | Temperature (° C.) Zone 1, 2, 3-8, 9, 10 | | | | Screw Speed (rpm) | Resin Rate (lb/h) | Reactant % of resin rate | Catalyst (ppm) | Torque (%) |
|---|---|---|---|---|---|---|---|---|---|
| 29 | 95 | 125 | 180 | 125 | 100 | 150 | 3 | 2.7%, 1,4-butanediol | 700, DBDA | 64 |
| 30 | 95 | 125 | 180 | 125 | 100 | 150 | 3 | 2.7%, 1-butanol | 700, DBDA | 61 |
| 31 | 95 | 125 | 180 | 125 | 100 | 150 | 3 | 2.7%, 1,4-butanediol | 700, DBDA | 59 |
| 32 | 95 | 125 | 180 | 125 | 100 | 150 | 3 | 2.7%, 1,4-butanediol | 700, TP | 64 |

1,4-butanediol and 700 ppm of titanium propoxide (TP) was injected into the extruder by an Eldex pump via a liquid injection port located at Barrel #4, at a total throughput of 3 pounds per hour. For Sample 30, ECOFLEX® F BX 7011 resin was fed into the extruder at Barrel #1 and a reactant solution of 2.7 wt. % of 1-butanol and 700 ppm of dibutylene

EXAMPLE 7

Fiber spinning was conducted with a pilot Davis Standard fiber spinning line consisting of two extruders, a quench chamber and a godet with a maximal speed of 3000 m/min. The spinning die plate used for these samples was a 16 holes plate with each hole with a diameter of 0.6 mm. Sample 29-32 were pre-dried at 70° C. before fiber spinning. Unmodified Ecoflex® F BX 7011 was also spun at an extruder speed of 5 rpm and 150° C. Extruder pressure rose quickly above 150° C. psi and shut off. No fiber was collected. Unmodified Ecoflex® F BX 7011 preblended with 20% PBS (Sample 25) was also spun at an extruder speed of 5 rpm, pressure of 2500 psi and temperature of 160° C. Fibers could only be drawn up to 200 m/min before break up. Fiber samples were analyzed on a MTS Synergie 200 tensile tester. The fiber spinning conditions and resulting fiber properties are shown in Table 12.

TABLE 12

Fiber spinning conditions and fibers properties of modified Ecoflex resins

| Samples No. | Godet speed m/min | Ext. Temp ° C. | Ext. speed rpm | Ext. press. Psi | Spin Die Temp ° C. | Diameter micron | Peak Load gf | Peak Stress Mpa | Strain at Break % | Denier | Tenacity |
|---|---|---|---|---|---|---|---|---|---|---|---|
| 29 | 1500 | 145 | 10 | 2225 | 135 | 24.3 | 4.12 | 88 | 104 | 5.3 | 0.8 |
| 30 | 1500 | 160 | 5 | 1300 | 160 | 16.8 | 2.4 | 105.4 | 103.1 | 2.5 | 0.96 |
| 31 | 2200 | 150 | 5 | 990 | 150 | 12.8 | 1.47 | 112.3 | 29.5 | 1.45 | 1.02 |
| 32 | 1500 | 160 | 10 | 2060 | 150 | 24.9 | 4.48 | 89.6 | 166.2 | 5.51 | 0.81 |

EXAMPLE 8

Bicomponent fibers with modified Ecoflex® F BX 7011 (Sample 28) as sheath and NatureWorks PLA 6201D as the core were also spun using the fiber spinning line of Example 7. The sheath/core ratios of the resulting bicomponent fibers for Sample 33 and Sample 34 were 20/80 and 30/70, respectively. Fiber spinning conditions are listed in Table 13.

TABLE 13

Fiber spinning conditions for making modified Ecoflex/PLA bicomponent fibers

| | Temperature (° C.) | | | | | | | Pressure | Melt Pump |
|---|---|---|---|---|---|---|---|---|---|
| | Zone 1 | Zone 2 | Zone 3 | Zone 4 | Zone 5 | Zone 6 | Zone 7 | Psi | rpm |
| Extruder 1 | 160 | 170 | 170 | 180 | 180 | 180 | 180 | 140 | 1-1.5 |
| Extruder 2 | 195 | 205 | 215 | 220 | 220 | 225 | 225 | 105 | 3.5-4 |

| | Lower SP | Upper SP | Chimney | Spinbeam |
|---|---|---|---|---|
| Quench Setpoints (° C.) | / | / | 100 | 240 |

| | Lower | Mid-Lower | Mid-Upper | Upper | Lower Air | Upper Air |
|---|---|---|---|---|---|---|
| Quench Readings (° C.) | 25 | 28 | 27 | 28 | 390 | 432 |
| Godet Speed (m/min) | 2500 | | | | | |

The resulting fibers were analyzed on a MTS Synergie 200 tensile tester. The properties are listed as in Table 14.

TABLE 14

Properties of modified Ecoflex and PLA bicomponent fibers

| Samples No. | Sheath (%) | Core (%) | Diamter (micron) | | Peak load (gf) | | Peak Stress (Mpa) | | Strain at Break (%) | | Denier | | Tenacity | |
|---|---|---|---|---|---|---|---|---|---|---|---|---|---|---|
| | | | Mean | SD | Mean | SD | Mean | SD | Mean | SD | Mean | SD | Mean | SD |
| 33 | 20 | 80 | 10.5 | 1 | 2.1 | 0.2 | 242 | 49 | 67.2 | 12.4 | 0.98 | 0.19 | 2.2 | 0.44 |
| 34 | 30 | 70 | 11 | 0.88 | 2 | 0.28 | 208 | 29 | 65.9 | 8.9 | 1.1 | 0.17 | 1.9 | 0.26 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:
1. A method for forming biodegradable, substantially continuous multicomponent filaments, the method comprising:
forming a first thermoplastic composition that contains a first polyester having a melting point of from about 150° C. to about 250° C.;
forming a second thermoplastic composition by melt blending a precursor aliphatic-aromatic copolyester with at least one alcohol so that the copolyester undergoes an alcoholysis reaction, the alcoholysis reaction resulting in a modified copolyester having a melt flow index that is greater than the melt flow index of the precursor copolyester, determined at a load of 2160 grams and temperature of 190° C. in accordance with ASTM Test Method D1238-E; and
co-extruding the first thermoplastic composition and the second thermoplastic composition to form substantially continuous filaments, wherein the first thermoplastic composition constitutes from about 5 wt. % to about 95 wt. % of the substantially continuous filaments and the second thermoplastic composition constitutes from about 5 wt. % to about 95 wt. % of the substantially continuous filaments.

2. The method of claim 1, wherein the ratio of the melt flow index of the modified copolyester to the melt flow index of the precursor copolyester is at least about 1.5.

3. The method of claim 1, wherein the ratio of the melt flow index of the modified copolyester to the melt flow index of the precursor copolyester is at least about 10.

4. The method of claim 1, wherein the modified copolyester has a melting point of from about 50° C. to about 150° C.

5. The method of claim 1, wherein the modified copolyester has a glass transition temperature of about 0° C. or less.

6. The method of claim 1, wherein the melt flow index of the modified copolyester is from about 5 to about 200 grams per 10 minutes.

7. The method of claim 1, wherein the melt flow index of the second copolyester is from about 15 to about 50 grams per 10 minutes.

8. The method of claim 1, wherein the modified copolyester is terminated with an alkyl group, hydroxyalkyl group, or a combination thereof.

9. The method of claim 1, wherein the modified copolyester has the following general structure:

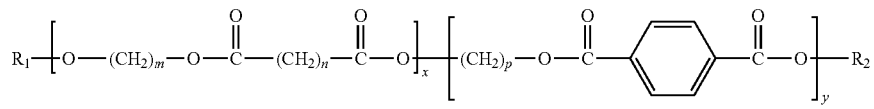

wherein,
m is an integer from 2 to 10, in some embodiments from 2 to 4, and in one embodiment, 4;
n is an integer from 0 to 18, in some embodiments from 2 to 4, and in one embodiment, 4;
p is an integer from 2 to 10, in some embodiments from 2 to 4, and in one embodiment, 4;
x is an integer greater than 1;
y is an integer greater than 1; and
$R_1$ and $R_2$ are independently selected from hydrogen; hydroxyl groups; straight chain or branched, substituted or unsubstituted $C_1$-$C_{10}$ alkyl groups; and straight chain or branched, substituted or unsubstituted $C_1$-$C_{10}$ hydroxalkyl groups.

10. The method of claim 9, wherein m and n are each from 2 to 4.

11. The method of claim 1, wherein the precursor copolyester is polybutylene adipate terephalate.

12. The method of claim 1, wherein the alcohol is employed in an amount of from about 0.1 wt. % to about 20 wt. %, based on the weight of the precursor copolyester.

13. The method of claim 1, wherein the alcohol is a monohydric alcohol, polyhydric alcohol, or a combination thereof.

14. The method of claim 1, wherein the alcohol is a polyhydric alcohol.

15. The method of claim 14, wherein the alcohol is a dihydric alcohol.

16. The method of claim 1, wherein a catalyst is employed to facilitate the alcoholysis reaction.

17. The method of claim 1, wherein melt blending occurs at a temperature of from about 50° C. to about 300° C. and an apparent shear rate of from about 100 seconds$^{-1}$ to about 10,000 seconds$^{-1}$.

18. The method of claim 1, wherein melt blending occurs at a temperature of from about 90° C. to about 220° C. and an apparent shear rate of from about 800 seconds$^{-1}$ to about 1200 seconds$^{-1}$.

19. The method of claim 1, wherein the first polyester is polylactic acid.

20. The method of claim 1, wherein the filaments have a sheath/core or side-by-side configuration.

21. A method for forming a nonwoven web, the method comprising randomly depositing the filaments of claim 1 onto a forming surface.

22. The method of claim 21, further comprising passing the web through a nip formed between two rolls to melt-fuse the filaments.

* * * * *